United States Patent
Kim

(10) Patent No.: US 7,902,165 B2
(45) Date of Patent: Mar. 8, 2011

(54) USE OF AIM3 ACTING AS A TUMOR SUPPRESSOR

(75) Inventor: Sunghoon Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 11/902,641

(22) Filed: Sep. 24, 2007

(65) Prior Publication Data

US 2008/0200382 A1    Aug. 21, 2008

Related U.S. Application Data

(62) Division of application No. 10/536,257, filed as application No. PCT/KR2004/002202 on Sep. 1, 2004, now abandoned.

(30) Foreign Application Priority Data

Apr. 27, 2004   (KR) .................. 10-2004-0029205

(51) Int. Cl.
*A61K 48/00* (2006.01)
(52) U.S. Cl. ........................................ 514/44
(58) Field of Classification Search .................. None
See application file for complete search history.

(56) References Cited

FOREIGN PATENT DOCUMENTS

WO    WO 99/46292    *   9/1999

OTHER PUBLICATIONS

Zips et al. (2005, In Vivo, 19:1-7).*
Rolland (Advanced Drug Delivery Reviews, 2005, 57:669-673).*
McNeish et al (Gene Therapy, 2004, 11:497-503).*
McCormick (Nature Reviews, 2001, 1:130-141).*
Park et al (Cell, 2005, 120:209-221).*
Rho et al., "Genetic dissection of protein-protein interactions in mult-tRNA synthetase complex," *Proc. Natl. Acad. Sci.*, 1999, vol. 96, pp. 4488-4493, National Academy of Sciences, Washington, D.C.
Ko et al., "Novel regulatory interactions and activities of mammalian tRNA synthetases," *Proteomics*, 2002, vol. 2, pp. 1304-1310, Wiley-VCH Verlag GmbH & Co., Germany.
Quevillon et al., "The p18 component of the multisynthetase complex shares a protein motif with the β and γ subunits of eukaryotic elongation fact 1," *FEBS Letters*, 1996, vol. 395, pp. 63-67, Elsevier Science BV, Amsterdam, Holland.
Mao et al., "Identification of genes expressed in human CD34+ hematopoietic stem/progenitor cells by expressed sequence tags and efficient full-length cDNA cloning," *Proc. Natl. Acad. Sci.*, 1998, vol. 95, pp. 8175-8180, National Academy of Sciences, Washington, D.C.

* cited by examiner

*Primary Examiner* — Laura B Goddard
(74) *Attorney, Agent, or Firm* — Buchanan Ingersoll & Rooney PC

(57) ABSTRACT

The present invention relates to novel uses of AIM3 acting as a tumor suppressor, and more particularly to methods for using an AIM3 protein or a nucleic acid encoding the protein to activate ATM or ATR and to treat ATM- or ATR-mediated diseases. The AIM3 protein according to the present invention interacts directly with ATM/ATR so as to activate ATM/ATR and proteins regulated by ATM/ATR. Also, the AIM3 protein upregulates tumor suppressor gene p53 and its target genes so as to not only inhibit the proliferation of cells but also to induce apoptosis.

4 Claims, 38 Drawing Sheets

Breast (B-95)

Seminal vesicle (B-103)

Lung (B-14)

Liver (B-207)

Lymph node (B-232)

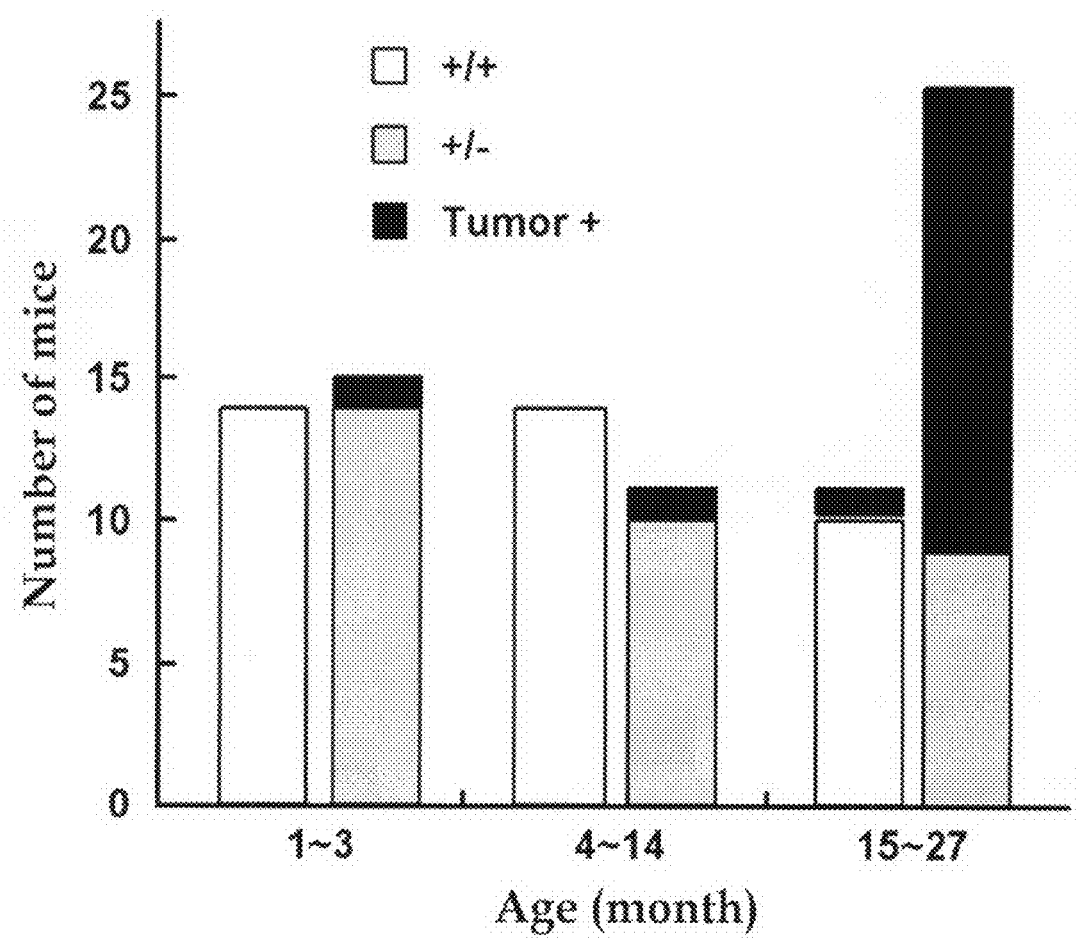

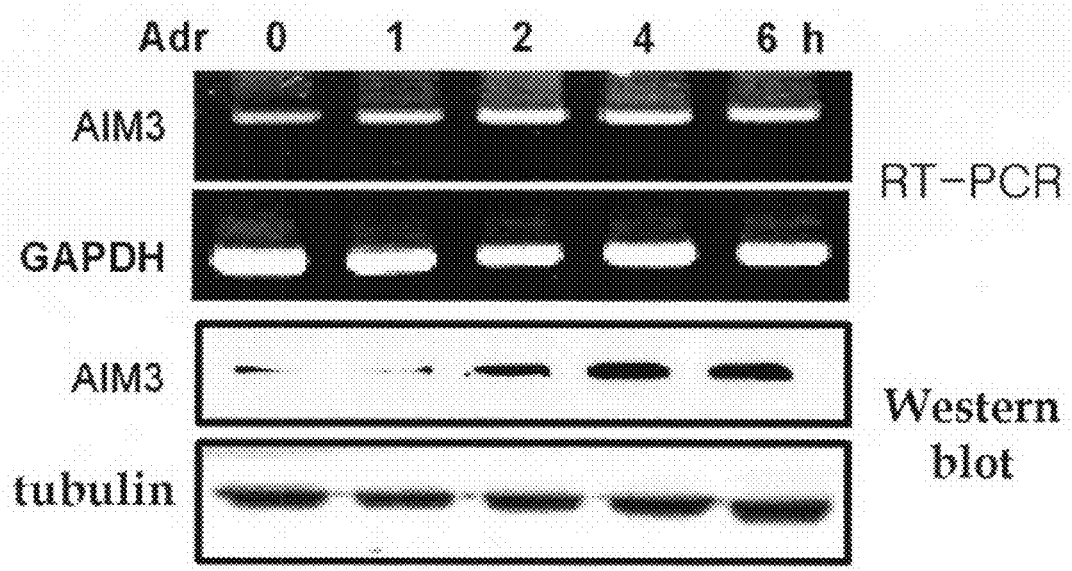

USE OF AIM3 ACTING AS A TUMOR SUPPRESSOR

CROSS-REFERENCE TO RELATED APPLICATIONS

This is a divisional of application Ser. No. 10/536,257, filed May 25, 2005, now abandoned, which is a 371 application of International Application No. PCT/KR04/02202, filed Sep. 1, 2004, which claims priority to KR 10-2004-0029205, filed Apr. 27, 2004, all of which are incorporated herein by reference.

TECHNICAL FIELD

The present invention relates to a novel tumor suppressor, and particularly to a novel tumor suppressor that activates ATM or ATR.

BACKGROUND ART

Cells have a variety of fail-safe mechanisms, one of which is to arrest the cell division of damaged chromosomal DNA and to repair the damage, thus preventing mutations from settling. When chromosomal DNA damaged by UV and the like is continued to undergo cell division in a condition where the damage is not repaired, the damaged chromosomal DNA will be replicated so as to accumulate mutations. This leads to an increase in the incidence of cancer cells. Accordingly, when DNA is damaged, cells operate a process of repairing the damage and an intracellular feedback mechanism of arresting the cell division until the repair of DNA damage is over, followed by inhibiting the development of cancers. Such a feedback mechanism is mediated by checkpoints in each cycle of cell division. The overall function of these checkpoints is to detect damaged or abnormally structured DNA and to coordinate cell-cycle progression with DNA repair (Robert T. *Genes & development*, 15:2177-2196, 2001). Typically, cell-cycle checkpoint activation slows or arrests cell-cycle progression, thereby allowing time for appropriate repair mechanisms to correct genetic lesions before they are passed on to the next generation of daughter cells. In certain cells, such as thymocytes, checkpoint proteins link DNA strand breaks to apoptotic cell death via the induction of p53 (Robert T. *Genes & development*, 15:2177-2196, 2001).

Cell-cycle checkpoints which are initiated by DNA damages are mainly regulated by ATM (ataxia-telangiectasia-mutated) and ATR (ATM- and Rad3-ralated) proteins (Shiloh, Y. *Curr. Opin. Gent. Dev.*, 11:71-77, 2001; Abraham, R. T. *Genes Dev.*, 15:2177-2196, 2001). Such proteins play a key role in the early signal transduction via the cell-cycle checkpoints. ATM- and ATR-deficient cells showed defects in arresting the cell cycle in response to radiation. Particularly, the ATM-deficient cells showed serious defects in G1, S and G2 checkpoints (Robert T. *Genes & development*, 15:2177-2196, 2001), and serious damages called "double strand breaks" occurred in the ATR -deficient cells. Furthermore, it was known that the incidence of tumor is greatly increased by the mutation of ATM/ATR.

ATM and ATR are highly homologous to each other and use the same substrate. However, they are different in that their activities are increased by different genotoxic stresses. ATM responds to agents, such as IR (ionizing radiation) that breaks double strands DNA, whereas ATR responds to agents (including IR) that cause bulky adducts on DNA or single strand DNA. Furthermore, ATM and ATR are activated by different methods. ATM activation requires autophosphorylation that results in the disruption of an ATM dimer (Bakkenist, C. J. et al., *Nature*, 421:499-506, 2003). How autophosphorylation of ATM triggered is still unknown. ATR may also be autophosphorylated, but it is not evident that ATR forms either an inactive dimer or an active monomer in cells. Also, it is not yet clear that other subunits or cofactors are required for the activation of ATM/ATR. In addition, the intracellular biochemical mechanism of a signal transduction system where the DNA damage causes the activation and operation of ATM/ATR was not completely established.

Target proteins known to be phosphorylated directly by ATM/ATR include p53, chk1, chk2, c-Abl, RPA and the like, of which p53 is phosphorylated on serine 15 by ATM/ATR. It was reported that the over-expression of p53 arrests G2 and suppresses the synthesis of two proteins, CDK1 (cyclin-dependent kinase 1) and cyclin BI, which are required for the entry of cells from G2 to M. Thus, p53 does not only the function of inhibiting the abnormal division and proliferation of cells, but also the function of arresting the cell cycle so as to repair the damaged DNA when DNA was damaged. Recently, the mutation and loss of p53 genes are recognized as one of the most frequent genetic mutations, which is found not only in any certain cancer but in almost all types of cancer in human. Moreover, p53 activates the transcription of p21, another tumor suppressor gene, thereby inhibiting the G1/S transition and causing the p53-dependent apoptosis. p21 which is expressed by p53 was known to be a kind of a CKI (cyclin -dependent kinase inhibitor) which functions to inhibit the division and proliferation of cells. Accordingly, efforts for developing new anticancer agents using cell-cycle regulation factors or substances of activating the factors are now continued.

Meanwhile, aminoacyl-tRNA synthetases (ARSs) which are important enzymes catalyzing the first step in protein synthesis are multifunctional proteins involved in various biological functions (Ko et al., *Proteomics*, 2:1304-1310, 2002). Among them, various mammalian tRNA synthetases, such as MRS (methionyl-tRNA synthetase), QRS (glutaminyl-tRNA synthetase), RRS (arginyl-tRNA synthetase), KRS (Lysyl-tRNA synthetase), DRS (aspartyl-tRNA synthetase) and so on, bind to three non-enzyme cofactors, designated as p43, p38 and p18, to form a macromolecular protein complex (Han et al., *Biochem. Biophys. Res. Commun.*, 303:985-993, 2003). Since ARSs are enzymes necessary for protein synthesis, this complex deems to be formed in order to facilitate protein synthesis.

Among the non-enzyme cofactors binding to ARSs, p43 is known to play an important role as a cytokine in immune response and angiogenesis (Ko et al., *J. Biol. Chem.*, 276: 23028-32303, 2001b; Park et al., *J. Biol. Chem.*, 277:45234-45248, 2002). Furthermore, p38 was found to downregulate c-myc, a protoocogene, and to be involved in lung differentiation (Kim et al., *Nat. Genet.*, 34:330-336, 2003). The last cofactor, p18, shows sequence homology to elongation factor subunits (EF-1) (Quevillon and Mirande, *FEBS Lett.*, 395:63-67, 1996). Given this, p18 is presumed to be involved in protein synthesis. However, the biological functions of p18 are not yet clearly understood, and particularly, there is no study on the relation between p18 and cancer.

DISCLOSURE OF THE INVENTION

Therefore, it is an object of the present invention to provide novel uses of a p18 (ARS-interacting multifunctional protein 3) protein.

The present inventors renamed p18 which had been known as a cofactor of an aminoacyl-tRNA synthetase (ARS) complex to "AIM3 (ARS-interacting multifunctional protein 3)". Accordingly, p18 will hereinafter be referred to as "AIM3".

To achieve the above object, in one aspect, the present invention provides a method for activating ATM, ATR and proteins regulated by ATM or ATR, in the cell, tissue and individual, comprising administering to the cell, tissue or individual an effective amount of one selected from the group consisting of the following:

(a) an isolated polypeptide of AIM3 (ARS-interacting multifunctional protein 3);

(b) an isolated polypeptide having at least 70% homology with the polypeptide (a); and (c) an isolated nucleic acid encoding the polypeptide (a) or (b).

In another aspect, the present invention provides a method for inducing the expression of p53 or its target genes in the cell, tissue or individual, comprising administering to the cell, tissue or individual an effective amount of one selected from the group consisting of following:

(a) an isolated polypeptide of AIM3 protein;

(b) an isolated polypeptide having at least 70% homology with the polypeptide (a); and (c) an isolated nucleic acid encoding the polypeptide (a) or (b).

In still another aspect, the present invention provides a method for inhibiting the proliferation of tumor cells, comprising administering to the cell, tissue or individual an effective amount of one selected from the group consisting of the following:

(a) an isolated polypeptide of AIM3 protein;

(b) an isolated polypeptide having at least 70% homology with the polypeptide (a); and (c) an isolated nucleic acid encoding the polypeptide (a) or (b).

In still another aspect, the present invention provides a method for stimulating apoptosis in the cell, tissue or individual, comprising administering to the cell, tissue or individual an effective amount of one selected from the group consisting of the following:

(a) an isolated polypeptide of AIM3 protein;

(b) an isolated polypeptide having at least 70% homology with the polypeptide (a); and (c) an isolated nucleic acid encoding the polypeptide (a) or (b).

In still another aspect, the present invention provides a method for treating or preventing ATM- or ATR-mediated diseases, comprising administering to a subject in need thereof an effective amount of one selected from the group consisting of the following:

(a) an isolated polypeptide of AIM3 protein;

(b) an isolated polypeptide having at least 70% homology with the polypeptide (a); and (c) an isolated nucleic acid encoding the polypeptide (a) or (b).

In still another aspect, the present invention provides a method for screening a substance having the effect of treating or preventing ATM- or ATR-mediated diseases, the method comprising the steps of:

(a) culturing AIM3 (ARS-interacting multifunctional protein 3) or a recombinant cell expressing the protein, together with a candidate substance; and (b) determining the effect of the candidate substance on an increase in the activity of AIM 3 or the intracellular level thereof.

In yet another aspect, the present invention provides a method for identifying a subject having the risk of ATM- or ATR-mediated diseases, comprising the steps of:

(a) measuring the expression level of ATM3 protein in tissue sampled from a subject; and (b) comparing the level of the AIM3 protein in the tissue with a normal AIM3 protein level.

In still another aspect, the present invention provides a kit for the diagnosis of ATM- or ATR-mediated diseases, comprising one selected from the group consisting of an AIM3 protein-encoding nucleic acid, a fragment thereof, a peptide encoded by the nucleic acid or its fragment, and an antibody to the peptide.

In another further aspect, the present invention provides pharmaceutical compositions comprising, as an active ingredient, one selected from the group consisting of the following:

(a) an isolated polypeptide of AIM3 protein;

(b) an isolated polypeptide having at least 70% homology with the polypeptide (a); and (c) an isolated nucleic acid encoding the polypeptide (a) or (b).

Hereinafter, the present invention will be described in detail.

In the present invention, novel activities of AIM3 (p18) known as a cofactor of an aminoacyl-tRNA synthetase (ARS) complex were identified. The physiological activities (functions) of AIM3 identified in the present invention are as follows:

First, in the DNA synthesis step and upon DNA damage, AIM3 is moved into nuclei and induced at a high level.

Second, AIM3 shows an anti-proliferation activity against cells.

Third, AIM3 induces apoptosis.

Fourth, AIM3 induces the expression of tumor suppressor gene p53 and its target genes.

Fifth, AIM3 interacts directly with ATM/ATR so as to activate ATM, ATR and proteins which are regulated by ATM or ATR.

Sixth, a reduction in the expression level of AIM3 induces tumorigenesis, and it is expressed at a low level in cancer cell lines and tissues isolated from cancer patients.

Accordingly, the present invention provides a method for activating one selected from the group consisting of ATM, ATR and proteins regulated by ATM or ATR using an AIM3 protein or a nucleic acid encoding the AIM3 protein.

As used herein, the term "activating" means the phosphorylation of proteins or the structural or chemical mutation of proteins. The activation of ATM/ATR is mediated by the biding of AIM3, which causes a variety of intracellular responses involved in ATM/ATR. Such intracellular responses include, but are not limited to, DNA repair, cell cycle regulation and apoptosis induction. Thus, the activation of ATM/ATR by AIM3 accompanies activation of downstream proteins which are involved in DNA repair signal transduction pathways induced by DNA replication or damage, a checkpoint signal transduction pathway in each cell cycle, and/or an apoptosis-inducing signal transduction pathway caused by DNA damage. The ATM/ATR-regulated proteins include proteins which are directly phosphorylated by ATM/ATR, and proteins which are sequentially phosphorylated in signal transduction pathways by the phosphorylation of said proteins. Preferred examples include, but are not limited to, H2AX (Burma S. et al., *J. Biol. Chem.*, 9; 276(45): 42462-42467, 2001), p53 (Saito S, et al., *J. Biol. Chem.*, 12; 277(15):12491-12494, 2002), chk2 (Matsuoka S, et al., *Proc. Natl. Acad. Sci.* U.S.A., 12; 97(19):10389-10394, 2000), chk1 (Kim S T et al., *J. Biol. Chem.*, 31; 274(53):37538-37543, 1999), BRCA1 (Xu B, et al., *Cancer Res.*, 15; 62(16): 4588-4591, 2002; Cortez D, et al., *Science*, 5; 286(5442): 1162-1166, 1999), c-Abl (Baskaran R, et al., *Nature*, 29; 387(6632):516-519, 1997), PHAS-1 (Chan D W et al., *J. Biol. Chem.*, 17; 275(11):7803-7810, 2000), RPA (Chan D W et al., *J. Biol. Chem.*, 17; 275(11):7803-7810, 2000), RAD9 (Chen M J et al., *J. Biol. Chem.*, 11; 276(19):16580-16586, 2001), MDM2 (Maya R, et al., *Genes Dev.*, 1; 15(9):1067-1077, 2001), MRE11 (Kim S T et al., *J. Biol. Chem.*, 31; 274(53): 37538-37543, 1999), Rad17 (Kim S T et al., *J. Biol. Chem.*, 31; 274(53):37538-37543, 1999), WRN (Kim S T et al. *J. Biol. Chem.*, 31; 274(53):37538-37543, 1999), PTS (Kim S T et al., *J. Biol. Chem.*, 31; 274(53):37538-37543, 1999), CtIP (Li S, et al., *Nature*, 13; 406(6792):210-215, 2000), eIF-4E binding protein 1 (Yang D Q, et al., *Nat. Cell. Biol.*, 2(12): 893-898, 2000), LKB1 (Sapkota G P, et al., *Biochem J.*, 1; 368(Pt 2):507-516, 2002), FANCD2 (Taniguchi T, et al., *Cell*, 17; 109(4):459-472, 2002), SMC1 (Yazdi P T, et al., *Genes Dev.*, 1; 16(5):571-582, 2002), Rad17 (Kim S T et al., *J. Biol. Chem.*, 31; 274(53):37538-37543, 1999), Nibrin (Kim S T et al., *J. Biol. Chem.*, 31; 274(53):37538-37543, 1999), NBS (Wu K. et al., *Nature*, 25; 405(6785):477-482, 2000), p95 (Kim S T et al., *J. Biol. Chem.*, 31; 274(53):37538-37543, 1999), Pin2/TRF1 (Kishi S. et al., *J. Biol. Chem.*, 3; 276(31): 29282-29291, 2001), DNA 5B (Kim S T et al., *J. Biol. Chem.*, 31; 274(53):37538-37543, 1999), BRCA2 (Kim S T et al., *J. Biol. Chem.*, 31; 274(53):37538-37543, 1999) and phosphatidylinositol 3-kinase (Kim S T et al., *J. Biol. Chem.*, 31; 274(53):37538-37543, 1999). More preferably, the proteins may be H2AX, p53 or chk2.

Furthermore, the present invention provides a method for inducing the expression of p53 or its target gene using the AIM3 protein or a nucleic acid encoding the AIM3 protein. As used herein, the term "p53-target gene" refers to a gene located in downstream of p53, whose expression is induced by p53. The p53-target gene may be a gene involved in at least one mechanism selected from the group consisting of p53 control, cell cycle regulation, DNA repair, apoptosis, angiogenesis, cellular stress response and determination of cell fate. Preferred examples of this target gene include, but are not limited to, p21 (Fujioka S, et al., *J. Biol. Chem.*, Apr. 21, 2004; Nayak B K, et al., *Oncogene*, 17; 21(47):7226-7229, 2002), PUMA (Gu J, et al., *Oncogene*, 12; 23(6):1300-1307, 2004; Yu J, et al., *Cell*, 7(3):673-682, 2001), GADD45 (Nayak B K, et al., *Oncogene*, 17; 21(47):7226-7229, 2002; el-Deiry W S., *Semin Cancer Biol.*, 8(5):345-57), 14-3-3 sigma (el-Deiry W S., *Semin Cancer Biol.*, 8(5):345-57), WIPI (Choi J, et al., *Genomics.*, 15; 64(3):298-306, 2000), mdm-2 (Freedman and Levine, *Cancer Research*, 59:1-7, 1999), EGFR (Tokino and Nakamura, *Crit. Rev. Onc. Hem.*, 33:1-6, 2000), PCNA (Tokino and Nakamura, *Crit. Rev. Onc. Hem.*, 33:1-6, 2000), Cyclin D1 (Tokino and Nakamura, *Crit. Rev. Onc. Hem.*, 33:1-6, 2000), Cyclin G (Tokino and Nakamura, *Crit. Rev. Onc. Hem.*, 33:1-6, 2000), TGFα (Inoue Y, et al., *Hepatology*, 36(2):366-344, 2002), BAX (Gu J, et al., *Oncogene*, 12; 23(6):1300-1307, 2004; Nayak B K, et al., *Oncogene*, 17; 21(47):7226-7229, 2002), BAK (Gu J, et al., *Oncogene*, 12; 23(6):1300-1307, 2004), FAS1 (Gu J, et al., *Oncogene*, 12; 23(6):1300-1307, 2004), Fas/APO1 (el-Deiry W S., *Semin Cancer Biol.*, 8(5):345-57), FASL (Mendoza-Rodriguez C A, et al., *Rev. Invest. Clin.*, 53(3):266-273, 2001), IGF-BP3 (Mendoza-Rodriguez C A, et al., *Rev. Invest. Clin.*, 53(3):266-273, 2001), PAG608 (Higashi Y, et al., *J. Biol. Chem.*, 1; 277(44):42224-42262, 2002), DR5/KILLER (Takimoto R, et al., *Oncogene*, 30; 19(14):1735-1743, 2000), GML (Higashiyama M, et al., *Eur. J. Cancer.*, 36(4):489-495, 2000; Nakamura Y., *Cancer Sci.*, 95(1):7-11, 2004), p53AIP1 (Nakamura Y., *Cancer Sci.*, 95(1):7-11, 2004), STAG1 (Nakamura Y., *Cancer Sci.*, 95(1):7-11, 2004), p53R2 (Nakamura Y., *Cancer Sci.*, 95(1):7-11, 2004), p53RFP (Nakamura Y., *Cancer Sci.*, 95(1):7-11, 2004), P2XM (Nawa G, et al. *Br. J. Cancer.*, 80(8):1185-1189, 1999), TSP-1 (Harada H, et al., *Cancer Lett.*, 28; 191(1):109-119, 2003), BAL1 (Nakamura Y., *Cancer Sci.*, 95(1):7-11, 2004), CSR (Nakamura Y., *Cancer Sci.*, 95(1):7-11, 2004), PIG3 (Giampieri S, et al., *Oncogene*, Apr. 12, 2004; Contente A, et al., *Nat. Genet.*, 30(3): 315-320, 2002), Apaf-1 (Giampieri S, et al., Oncogene, Apr. 12, 2004), p53RDL1 (Nakamura Y., *Cancer Sci.*, 95(1):7-11, 2004), Staf50 (Obad S, et al., *Oncogene*, 20; 23(3):4050-4059, 2004), CD200 (Rosenblum Md., et al., *Blood*, 1; 103 (7):2691-2698, 2004) and Snk/PIk2 (Burns T F, et al., *Mol. Cell. Biol.*, 23(16):5556-5571, 2003). More preferably, the target gene may be p21 or PUMA.

AIM3 of the present invention inhibits the proliferation of tumor cells through signal transduction pathways mediated by ATM/ATR and stimulates apoptosis caused by DNA damage. Accordingly, the present invention provides methods to inhibit the proliferation of tumor cells and to stimulate apoptosis, using the AIM3 protein and a nucleic acid encoding the AIM3 protein.

All the methods described above comprise administering an effective amount of the AIM3 protein or the nucleic acid encoding the protein to cells or tissues. As used herein, the term "effective amount" refers to the amount of AIM3, which shows an effect selected from the group consisting of the following: the activation of ATM/ATR in cells or tissues; the increase of phosphorylation of ATM/ATR-regulated proteins; the induction of expression of p53 or its target gene; the inhibition of proliferation of tumor cells; and the promotion of apoptosis.

The AIM3 proteins used in the present invention include natural or recombinant AIM3 proteins, or proteins having the substantially equivalent physiological activity of the natural or recombinant AIM3 proteins. The amino acid sequence of the AIM3 protein is known in the art and preferably derived from mammals, including human beings. The AIM3 protein of the present invention preferably has an amino acid sequence shown in SEQ ID NO: 1. Proteins having the substantially equivalent physiological activity of AIM3 include natural/recombinant AIM3 proteins, their functional equivalents and their functional derivatives. As used herein, the term "the substantially equivalent physiological activity" means the activity of: activating ATM/ATR or ATM/ATR-regulated proteins; inducing the expression of p53 or its target gene; inhibiting the proliferation of tumor cells; and/or stimulating apoptosis. The term "functional equivalents" refers to amino acid sequence variants with a substitution of some or all of the amino acids of a natural AIM3 protein or a deletion or addition of some of the amino acids, which have a physiological activity substantially equivalent to the natural AIM3 protein. Furthermore, the term "functional derivatives" refers to those having a physiological activity substantially equivalent to natural AIM3 protein, as proteins modified to increase or reduce the physicochemical properties of the AIM 3 protein. The proteins having a physiological activity substantially equivalent to the AIM3 protein have a homology of at least 70%, preferably at least 80%, and more preferably at least 90%, with the polypeptide shown in SEQ ID NO: 1. The AIM3 protein used in the present invention can be prepared by any genetic engineering method known in the art.

The inventive pharmaceutical composition containing the AIM3 protein as an active ingredient can be administered to human beings and animals by oral route or by parenteral route, such as an intravenous, subcutaneous, intranasal or intraperitoneal route. Oral administrations include sublingual application. Parenteral administrations include injection techniques, such as subcutaneous injection, intramuscular injection and intravenous injection, as well as drip infusion. In addition, the pharmaceutical composition can be formulated into various forms with a pharmaceutically acceptable carrier by a conventional method. As used herein, the term "pharmaceutically acceptable" carrier means a substance which is physiologically acceptable and, when administered to human beings, generally does not cause allergic reactions, such as gastrointestinal disorder and dizziness, or similar reactions thereto.

As the pharmaceutically acceptable carriers, in the case of oral administration, there may be used binders, lubricants, disintegrants, excipients, solubilizers, dispersing agents, stabilizers, suspension agents, pigments and flavors, and in case of injection agent, there can be used buffers, preservatives, analgesics, solubilizers, isotonics and stabilizers, and in case of formulations for local administration may include bases, excipients, lubricants and preservatives. As described above, the inventive pharmaceutical composition containing the AIM3 protein may be formulated into various forms with the pharmaceutically acceptable carriers. For example, for oral administration, the inventive composition may be formulated into the form of tablets, troches, capsules, elixirs, suspensions, syrups, wafers and so on, and for injection agent, it may be formulated into unit dose ampoules or multiple dose products.

A total effective amount of the AIM3 protein of the present invention can be administered to patients in a single dose or can be administered by a fractionated treatment protocol, in which multiple doses are administered over a more prolonged period of time. Although the amount of the AIM3 protein or a nucleic acid encoding the AIM3 protein in the inventive pharmaceutical composition may vary depending on the severity of diseases, the protein or the nucleic acid may be generally administered several times a day at an effective dose of 1 μg-10 mg. However, a suitable dose of the AIM3 protein in the inventive pharmaceutical composition may depend on many factors, such as the age, body weight, health condition, sex, disease severity, diet and excretion of patients, as well as the route of administration and the number of treatments to be administered. In view of these factors, any person skilled in the art may determine an effective dose for treating or preventing ATM/ATR-mediated diseases. The inventive pharmaceutical composition containing the AIM3 protein has no special limitations on its formulation, administration route and/or administration mode insofar as it shows the effects of the present invention.

Meanwhile, nucleic acids encoding the AIM3 protein of the present invention include DNA or RNA. Preferably, they refer to DNA encoding AIM3 proteins derived from mammals, particularly human beings. The human AIM3 gene is known in the art (GenBank accession No. AB011079). Preferably, the nucleic acid of the present invention is shown in SEQ ID NO: 2. The nucleic acids also include nucleic acids encoding functional equivalents to the AIM3 protein. The present invention can be included nucleic acids having a sequence homology of at least 80%, preferably at least 90%, and more preferably at least 95% with either a nucleic acid encoding the AIM3 protein or a nucleic acid comprising the complementary nucleotide sequence thereof.

The nucleic acid encoding the AIM3 protein may be used for gene therapy by inserting it into an expression vector, such as a plasmid or viral vector, and then introducing the expression vector into a target cell by any method known in the art, such as infection or transduction.

A gene transfer method using a plasmid expression vector is a method of transferring a plasmid DNA directly to human cells, which is an FDA-approved method applicable to human beings (Nabel, E. G., et al., *Science,* 249:1285-1288, 1990). Unlike viral vectors, the plasmid DNA has an advantage of being homogeneously purified. Plasmid expression vectors which can be used in the present invention include mammalian expression plasmids known in the pertinent art. For example, they are not limited to, but typically include pRK5 (European Patent No. 307,247), pSV16B (PCT Publication No. 91/08291) and pVL1392 (PharMingen).

The plasmid expression vector containing the nucleic acid according to the present invention may be introduced into target cells by any method known in the art, including, but not limited to, transient transfection, microinjection, transduction, cell fusion, calcium phosphate precipitation, liposome-mediated transfection, DEAE dextran-mediated transfection, polybrene-mediated transfection, electroporation, gene gun methods, and other known methods for introducing DNA into cells (Wu et al., *J. Bio. Chem.,* 267:963-967, 1992; Wu and Wu, *J. Bio. Chem.,* 263:14621-14624, 1988).

In addition, virus expression vectors containing the nucleic acid according to the present invention include, but are not limited to, retrovirus, adenovirus, herpes virus, avipox virus and so on.

The retroviral vector is so constructed that non-viral proteins can be produced within the infected cells by the viral vector in which virus genes are all removed or modified. The main advantages of the retroviral vector for gene therapy are that it transfers a large amount of genes into replicative cells, precisely integrates the transferred genes into cellular DNA, and does not induce continuous infections after gene transfection (Miller, A. D., *Nature,* 357:455-460, 1992). The retroviral vector approved by FDA was prepared using PA317 amphotropic retrovirus packaging cells (Miller, A. D. and Buttimore, C., *Molec. Cell Biol.,* 6:2895-2902, 1986).

Non-retroviral vectors include adenovirus as described above (Rosenfeld et al., *Cell,* 68:143-155, 1992; Jaffe et al., *Nature Genetics,* 1:372-378, 1992; Lemarchand et al., *Proc. Natl. Acad. Sci. USA,* 89:6482-6486, 1992). The main advantages of adenovirus are that it transfers a large amount of DNA fragments (36 kb genomes) and is capable of infecting non-replicative cells at a very high titer. Moreover, herpes virus may also be useful for human genetic therapy (Wolfe, J. H., et al., *Nature Genetics,* 1:379-384, 1992). In addition, any suitable virus vector known in the art may be used.

A vector capable of expressing the AIM3 gene may be administered by a known method. For example, the vector may be administered locally, parenterally, orally, intranasally, intravenously, intramuscularly or subcutaneously, or by other suitable routes. Particularly, the vector may be injected directly into a target cancer or tumor cell at an effective amount for treating the tumor cell of a target tissue. Particularly for a cancer or tumor present in a body cavity such as in the eye, gastrointestinal tract, genitourinary tract, pulmonary and bronchial system and so on, the inventive pharmaceutical composition can be injected directly into the hollow organ affected by the cancer or tumor using a needle, a catheter or other delivery tubes. Any effective imaging device, such as X-ray, sonogram, or fiberoptic visualization system, may be used to locate the target tissue and guide the needle or catheter tube. In addition, the inventive pharmaceutical composition comprising the nucleic acid encoding the AIM3 protein may be administered into the blood circulation system for treatment of a cancer or tumor which cannot be directly reached or anatomically isolated.

The pharmaceutical composition comprising the nucleic acid encoding the AIM3 protein as an active ingredient may additionally comprise pharmaceutically acceptable carriers or excipients. These carriers or excipients include dispersing agents, wetting agents, suspending agents, diluents and fillers. The ratio of the particular pharmaceutically acceptable carrier and the expression vector contained in the inventive pharmaceutical composition can be determined by the solubility and chemical properties of the composition, and the particular administration mode. The therapeutic or preventive effective amount of the inventive pharmaceutical composition containing the AIM3 protein-encoding nucleic acid may be suitably selected depending on the subject to be administered, age, individual variation and disease condition.

In another aspect, the present invention provides a method for treating or preventing ATM/ATR-mediated diseases using the AIM3 protein or a nucleic acid encoding the AIM3 protein. Specifically, the present invention provides a method for treating or preventing ATM- or ATR-mediated diseases, which comprise administering to a subject requiring treatment an effective amount of one selected from the group consisting of the following: (a) an isolated polypeptide of an AIM3 protein; (b) a polypeptide having at least 70% homology with the polypeptide (a); and (c) an isolated nucleic acid encoding the polypeptide (a) or (b). As used herein, the term "subject" means mammals, particularly animals including human beings. The subject may be a patient requiring treatment. Furthermore, the term "ATM- or ATR-mediated diseases" refers to diseases induced by the inactivation or activation reduction of ATM/ATR, i.e., diseases induced by abnormalities occurring in signal transduction pathways mediated by ATM/ATR, due to the inactivation or activation reduction of ATM/ATR. The signal transduction pathways mediated by ATM/ATR include signal transduction pathways mediated by ATM/ATR themselves or ATM/ATR-regulated proteins. The signal transduction pathways may be signal transduction pathways in DNA repair, cell cycle regulation, apoptosis, p53 regulation, angiogenesis and/or intracellular stress response. The ATM/ATR-mediated diseases may be caused by the over-proliferation of cells, such as cancers or psoriasis. The cancers include, but are not limited to, breast cancer, rectal cancer, lung cancer, small-cell lung cancer, stomach cancer, liver cancer, blood cancer, bone cancer, pancreatic cancer, skin cancer, head or neck cancer, skin or intraocular melanoma, uterine carcinoma, ovarian cancer, colorectal cancer, cancer near the anus, colon cancer, oviduct carcinoma, endometrial carcinoma, cervical cancer, vaginal cancer, vulva carcinoma, Hodgkin's disease, esophagus cancer, small intestinal tumor, endocrine gland cancer, thyroid cancer, parathyroid cancer, adrenal cancer, soft-tissue sarcoma, uterine cancer, penis cancer, prostate cancer, chronic or acute leukemia, lymphocytic lymphoma, bladder cancer, kidney or urethra cancer, kidney cell carcinoma, kidney pelvis carcinoma, CNS tumor, primary CNS lymphoma, spinal tumor, brain stem glioma, and pituitary adenoma, and a combination of one or more thereof. Particularly, the treating or preventing method according to the present invention is effective in treating or preventing cancers caused by p53 gene abnormalities. In this method, the dose (effective amount) and administration mode of the AIM3 protein or the nucleic acid encoding the AIM3 protein are the same as described above.

The AIM3 protein of the present invention interacts directly with ATM/ATR so as to activate ATM/ATR and various proteins regulated by ATM/ATR. Particularly, the AIM3 protein shows the activity of inducing the expression of p53, one of the ATM/ATR-regulated proteins, and the expression of its target genes, so as to stimulate the apoptosis of cells for DNA damage and to inhibit the proliferation of tumor cells. Such characteristics of AIM3 may be used to screen a substance effective for treating/preventing ATM/ATR-mediated diseases, particularly cancer. Accordingly, the present invention provides a method for screening a substance effective for treating or preventing ATM/ATR-mediated diseases, which comprise the step of: (a) culturing the AIM3 protein or a recombinant cell expressing the AIM3 protein together with a candidate substance; and (b) determining the effect of the candidate substance on an increase in the activity of AIM3 or the intracellular level thereof. As used herein, the term "activity of the AIM3 protein" refers to the binding activity with ATM/ATR, the activity of promoting the phosphorylation of ATM/ATR or proteins regulated by ATM/ATR, and/or the activity of inducing the expression of p53 and its target genes. The term "increase in the intracellular level of the AIM3 protein" means the increase in the concentration of the AIM3 protein by the increase of expression of the AIM3 gene or the inhibition of the degradation of the AIM3 proteins.

The expression of the AIM3 gene includes process for the transcription of the AIM3 gene and the translation into proteins. Accordingly, the substances screened in the present invention has the property of: promoting the binding of AIM3 to ATM/ATR; activating ATM/ATR or proteins regulated by ATM/ATR; inducing the expression of p53 and its target genes; and/or increasing the intracellular level of the AIM3 protein. These substances include not only proteins but also naturally occurring or chemically synthesized compounds or extracts.

The activity and intracellular level of the AIM3 protein can be measured by various methods known in the art. Exemplary methods include, but are not limited to, co-immunoprecipitation, enzyme-linked immunosorbent assay, radioimmunoassay (RIA), immunohistochemical assay, Western blotting, and fluorescence activated cell sorter (FACS) analysis.

In addition, for the screening method using the AIM 3 of the invention as a target gene, high throughput screening (HTS) can be applied. The HTS is a method for screening the biological activities of a number of candidate substances simultaneously or almost simultaneously by testing the candidate substances simultaneously. In a certain embodiment, cell lines are cultured in a 96-well microtiter plate or a 192-well microtiter plate, into which a number of candidate substances are added and then measured for the expression of AIM3 by an immunohistochemical method. In this format, 96 independent tests may be simultaneously performed in a single 8 cm×12 cm plastic plate containing 96 reaction wells. The wells require an assay volume of 50-500 µl typically. In addition to the plate, a number of gauges, instruments, pipetters, robots, plate washers and plate readers are commercially available in order to make the 96-well format suitable for a wide range of homogeneous and heterogeneous assays.

Meanwhile, the expression level of the AIM3 gene or protein in biological samples (e.g., blood, serum, sputum, urine and/or tumor biopsies) collected from subjects can be compared with that of normal persons so as to diagnose (identify) subjects having the risk of ATM/ATR-mediated diseases. Specifically, using one selected from the group consisting of an AIM3 protein-encoding nucleic acid, a fragment thereof, a peptides encoded by them, and an antibody to the peptide as a primer or probe, ATM/ATR-mediated diseases may be identified. Accordingly, the present invention provides a method for identifying a subject having the risk of ATM/ATR-mediated diseases, which comprise the steps of: (a) measuring the expression level of AIM3 in a tissue sampled from a subject; and (b) comparing the level of AIM3 in the tissue with a normal AIM3 level. The methods for identifying such a disease include those which are capable of detecting the expression of AIM3 at a transcriptional or translational level (such as RT-PCR, Northern blotting, Western blotting, immunological assays and so on). This method is very effective for diagnosing cancer among ATM/ATR-mediated diseases.

In still another aspect, the present invention provides a kit for the diagnosis of ATM/ATR-mediated diseases, which comprises one selected from the group consisting of a AIM3-encoding nucleic acid, a fragment thereof, a peptide encoded by them, and an antibody to the peptide. The AIM3 protein-encoding nucleic acid and a fragment thereof may be synthesized with reference to the known sequence of the AIM3 gene. The fragment of nucleic acid is preferably a primer capable of amplifying the AIM3 gene. The peptide encoded by the AIM3 protein-encoding nucleic acid or its fragment may be synthesized by any technique known in the art (Creighton, *Proteins: Structures and Molecular Principles*, W.H. Freeman and Co., NY, 1983). The peptide can be produced by the conventional stepwise liquid or solid phase synthesis, fragment condensation, F-MOC or T-BOC chemistry (Williams et al., Eds., *Chemical Approaches to the Synthesis of Peptides and Proteins*, CRC Press, Boca Raton Fla., 1997; Atherton & Sheppard, Eds., *A Practical Approach*, IRL Press, Oxford, England, 1989).

The antibody to the peptide can be produced using the AIM3 protein or its fragment as an antigen by any conventional method widely known in the immunological field. The antibodies include polyclonal antibodies and monoclonal antibodies.

The polyclonal antibodies can be prepared from a variety of warm-blooded animals, such as horses, cattle, goats, sheep, dogs, fowl, turkeys, rabbits, mice or rats, by any conventional technique known in the art. Namely, the animals are immunized by intraperitoneal, intramuscular, intraocular or subcutaneous injection of an antigen. The immunogenicity to the antigen can be increased by the use of an adjuvant, for example Freund's complete adjuvant or incomplete adjuvant. Following booster immunization, a small serum sample was collected and tested for the reactivity to the target antigen. Once the animal's titer reaches a stagnant state in view of its reactivity to the antigen, a large amount of the polyclonal antibodies can be obtained by bleeding the animal at one-week intervals or by blood-letting the animal.

The monoclonal antibodies can also be produced by a known method (Kennettm McKearn, and Bechtol (eds.), *Monoclonal Antibodies, Hybridomas; A New Dimension in Biological Analyses*, Plenum Press, 1980). The monoclonal antibodies can be produced by immunizing an animal with the AIM3 protein or its fragment as an immunogen, fusing the splenocytes of the immunized animal with myeloma cells to produce a hybridomas, screening a hybridoma that selectively recognizes the AIM3 protein, culturing the screened hybridoma, and isolating antibodies from the hybridoma culture. Alternately, the monoclonal antibodies according to the present invention may also be prepared by injecting said hybridoma into an animal, and after a given period of time, isolating antibodies from the collected ascites of the animal.

The antibody contained in the inventive diagnostic kit is preferably immobilized onto a solid substrate. The antibody can be immobilized by various techniques described in literatures (*Antibodies*: A Laboratory Manual, Harlow & Lane; Cold SpringHarbor, 1988). Suitable solid substrates include those supported by rods, synthetic glass, agarose beads, cups, flat packs, or other solid support or those having a film or coating attached to them. In addition, other solid substrates include cell culture plates, ELISA plates, tubes and polymeric films.

The diagnostic kit according to the present invention may contain, in addition to an antibody selectively recognizing the AIM3 protein, reagents which are used in immunological assays. The immunological assays may include methods capable of measuring the binding of an antigen to the antibody of the present invention. These methods are known in the art and include, for example, immunocytochemical assays, immunohistochemical assays, radioimmunoassays, ELISA (enzyme linked immunoabsorbent assay), immunoblotting, Farr assays, precipitin reaction, turbidimetry, immunodiffusion, counter-current electrophoresis, single radical immunodiffusion and immunofluorescence.

Reagents which are used in the immunological assays include a suitable carrier, a labeling substance capable of emitting detectable signals, a solubilizer and a washing agent. Furthermore, if the labeling substance is enzyme, a substrate capable of measuring enzymatic activity and a reaction stopping agent may be used.

Suitable carriers include, but are not limited to, soluble carriers, for example, one of biologically acceptable buffers known in the art (e.g., PBS), insoluble carriers, for example polystyrene, polyethylene, polypropylene, polyester, polyacrylonitrile, fluorine resin, crosslinked dextran, polysaccharide, polymers, such as latex containing magnetic fine particles plated with metal, paper, glass, metal, agarose and combinations thereof.

Labeling substances capable of emitting detectable signals include enzymes, fluorescent substances, luminescent substances and radioactive substances. The enzymes include peroxidase, alkaline phosphatase, β-D-galactosidase, glycose oxidase, maleate dihydrogenase, glucose-6-phosphodihydrogenase, invertase and so on. The fluorescent substances include fluorescein isothiocyanate and phycobili-protein. As luminescent substances, isolucinol and lucigenin and so on can be used. And, as radioactive substances, $I^{131}$, $C^{14}$, $H^3$ and so on, can be used. However, the above examples are only examples and anything used in immunoassay can be used. The ATM/ATR-mediated diseases which can be diagnosed with the inventive kit are the same as described above, and preferably, may be lung cancer, colon cancer, liver cancer, lymphoma and leukemia.

In one embodiment of the present invention, in order to identify the biological functions of AIM3, AIM3 gene-deficient mice were produced by a gene trap method. Then, genomic DNA mutated by the insertion of a gene trap vector was introduced into the embryonic stem cell of the mice so as to construct a mutant library. Clones containing the mutated AIM3 gene were searched from the library and used to prepare AIM3 heterozygous mutant mice.

In another embodiment of the present invention, the sequence of an AIM3 allele in the mutant mice was analyzed. The results showed that the gene trap vector was integrated between the first and second exons in the AIM3 gene (see FIG. 1*a*). Furthermore, genomic PCR and Southern blotting were performed to determine AIM3 mutation (FIGS. 1*b* and 1*c*), and the expression level of AIM3 by the mutation was determined using Western blot (see FIG. 1*d*).

The post-natal genotype of progenies obtained by cross-breeding the AIM3 heterozygous mutant mice (hereinafter, referred to as "AIM3$^{+/-}$ mice") and the genotype of embryos with the passage of time were examined and the results showed that the AIM3$^{+/-}$ mice appeared at a similar ratio to that of wild-type littermates (see Table 1). This indicates that about 50% of the AIM3$^{+/-}$ mice were dead in the pre-natal stage. AIM3 homozygous mice (hereinafter, referred to as "AIM3$^{-/-}$ mice") would die during the early embryonic stage (see Tables 1 and 2). This suggests that AIM3 performs an important role in vivo. Particularly, considering that the genetic eradication of proteins, such as Rad51, Chk1/2 and ATR involved in the DNA-damaging response and repair system, causes early embryonic lethality (de Klein et al., *Curr. Biol.*, 10:479-482, 2000; Lim and Hasty, *Mol. Cell Biol.*, 14:7133-7143, 1996; Takai et al., *Genes Dev.*, 14:1439-1447, 2000), it was believed that AIM3 would be involved in the DNA-damaging response and repair system.

Since the AIM3 protein is related to a multi-tRNA synthetase complex involved in protein synthesis (Han et al., *Biochem. Biophys. Res. Commun.*, 303:985-993, 2003), the inventors expected that a reduction of the AIM3 level would have an effect on the overall body growth of mice. However, it was interestingly shown that the growth rate of the AIM3$^{+/-}$ mice was similar to or slightly higher than that of wild-type mice regardless of their sex (data not shown). This suggests that protein synthesis is not inhibited by a reduction of the AIM3 level.

In another embodiment of the present invention, we examined the histological characteristics of tissues and organs isolated from the AIM3$^{+/-}$ mice in order to identify the function of the AIM3 gene. The results showed that various tumors were found in the tissues and organs isolated from the AIM3$^{+/-}$ mice, and the incidence of the tumors was significantly increased when their age passed over 15 months (see FIGS. 2a to 2c and Table 3). Particularly, in the AIM3$^{+/-}$ mice, lymphomas have developed at a high frequency (see Table 3). This is consistent with the previous report that the loss of DNA repair functions can evoke lymphomas (Bassing et al., *Cell*, 114:359-370, 2003; Celeste et al., *Cell*, 114:371-383, 2003). From the result that various tumors spontaneously formed in the AIM3-deficient mice, it is suggested that AIM3 is a powerful tumor suppressor involved in the tumorigenic pathway.

A rapid cell cycle is a typical indication for tumorigenesis (Evan and Vousden, *Nature*, 411:342-348, 2001). Thus, in another embodiment of the present invention, we examined whether AIM3 is involved in cell cycle control. As a result, cells isolated from the AIM3-deficient mice increased faster than those of wild-type mice and showed faster cell cycle (see FIGS. 3a and 3b). Furthermore, the expression of AIM3 in cell cycles was examined by Western blot analysis and flow cytometry, and the results showed that AIM3 was significantly induced during DNA synthetic phase (see FIGS. 3c and 3d). To understand the functional reason for the AIM3 induction during DNA synthetic phase, the cellular localization of AIM3 in growth arrest state and proliferation condition was examined. According to the results, AIM3 was detected mainly in cytoplasm when the cell growth was suppressed by serum starvation. However, it was detected in nucleus when the cells resumed growth (see FIG. 3e). This indicates that, during DNA synthesis, AIM3 is not only induced but also translocated into nuclei. Such results suggest that AIM3 can perform novel functions within the nuclei.

Cell responses to DNA damage include cell cycle arrest, apoptosis, and direct activation of DNA repair networks (Zhou B B et al., *Cancer Biol. Ther.*, S (4 Suppl 1):S16-22, 2003). Also, the resistance to apoptosis, one of cell responses, is a typical indication for tumorigenesis (Evan and Vousden, *Nature*, 411:342-348, 2001). Thus, in order to examine whether AIM3 is involved in apoptosis regulation, the response of AIM3$^{+/-}$ mouse-derived cells was examined using adriamycin that induces DNA damage. The AIM3$^{+/-}$ mouse-derived cells show the resistance to apoptosis (see FIG. 4a). Moreover, the growth of wild-type mouse cells was completely arrested by adriamycin, whereas that of the AIM3$^{+/-}$ mouse-derived cells was slightly inhibited (see FIG. 4b). A change in the AIM3 level caused by DNA damage was examined and the results showed that the expression of AIM3 was induced at both transcriptional and translational levels by treatment with a DNA-damaging agent such as adriamycin (see FIG. 4c). In addition, the cellular localization of AIM3 caused by DNA damage was examined. The results showed that nuclear foci formed by AIM3 were remarkably increased in UV-irradiated cells (see FIG. 4d). All of these results suggest that AIM3 is involved in the responses to DNA damage induced by genotoxic stress, and it is translocated into the nuclei when DNA is damaged.

In still another embodiment of the present invention, it was examined whether AIM3 is involved in cell proliferation. The results showed that cells and tissues derived from the AIM3-deficient mice had a cell proliferation rate higher than those of wild-type mouse cells (see FIGS. 5a and 5b). In addition, the level of proliferation of cells transfected with the AIM3 gene was lower than that of wild-type mouse cells (see FIG. 5c). This suggests that AIM3 shows the anti-proliferation activity against tumor cells.

According to the above results indicating that AIM3 is induced at a high level during DNA synthetic phase and when DNA get damaged, and has anti-proliferation activity similar to other DNA repair proteins (Falck et al., *Nature*, 410:842-847, 2001; Lim et al., *Mol. Cell*, 7:683-694, 2000), it can be found that AIM3 is functionally involved in signal transduction pathways that respond to the repair of DNA damage caused by the DNA replication or stress.

Meanwhile, it is known that p53, a tumor suppressor gene, does functions of not only inhibiting the abnormal division and proliferation of cells but also arresting the cell cycle in the case of cellular DNA damage so as to repair the damaged DNA, and p53 is involved in cell proliferation and apoptosis to prevent DNA from being unlimitedly amplified (Levine, *Cell*, 88:323-331, 1997; Vousden, *Cell*, 103:691-694, 2000). Thus, the inventors examined the functional connection between AIM3 and p53. The results showed that, in cells transfected with the AIM3 gene, the levels of not only p53 but also its target gene, p21, were increased (see FIGS. 6a and 6b). This increase in the gene level was further increased by treatment with adriamycin that induces apoptosis (see FIG. 6c). The level of proliferation of the AIM3 gene-transfected cells was lower than that of wild-type cells, and anti-proliferation activity of AIM3 was abolished in p53- or p21-deficient cancer cells (see FIG. 6d). The induction of p53 by UV or adriamycin was blocked when AIM3 was suppressed (see FIG. 6e). This indicates that AIM3 upregulates the expression of p53 induced by DNA damage and its target gene p21, thus inhibiting the proliferation of cancer cells.

It is known that mammalian ATM and ATR playing a key role in cell cycle checkpoints initiated by DNA damage are serine-threonine kinases which are involved in DNA repair processes responding to other genotoxic stresses (Yang et al. *Carcinogenesis*, 24: 1571-1580, 2003). Furthermore, ATM and ATR not only activate directly p53 in response to DNA damage but also regulate the cell cycle via p53 (Abraham, *Genes Dev.*, 15:2177-2196, 2001). Thus, in order to examine whether AIM3 regulates p53 via ATM/ATR, the present inventors examined whether ATM/ATR inhibitors inhibit the activity of AIM3. The results indicated that the anti-proliferation activity of AIM3, the apoptosis induced by AIM3, and the AIM3-dependent expression of p53, were all inhibited by caffeine, inhibitor of ATM/ATR (see FIGS. 7a to 7c). Moreover, the AIM3-dependent expression of p53 was also blocked by the expression of the kinase-dead domain of ATM (KD-ATM) that inhibits specifically the activity of ATM (see FIG. 7d). These results suggest that AIM3 acts through ATM/ATR.

In order to examine the relation between AIM3 and ATM/ATR in more detail, the present inventors analyzed the interaction between AIM3 and ATM/ATR. The results indicated that the interaction between the AIM3 and ATM/ATR was enhanced by stresses, such as the exposure to UV, adriamycin treatments, etc., and the interaction was done by the specific binding of AIM3 to the FAT domain of ATM/ATR (FIGS. 8a to 8c).

Then, the present inventors examined whether the activity of ATM/ATR is enhanced by the association with AIM3. The results showed that the phosphorylation level of H2AX in the AIM3$^{+/-}$ mouse-derived cells, which is a substrate for ATM/ATR, was significantly lower than that of H2AX in wild-type mouse cells (see FIG. 9a). Furthermore, the phosphorylation of H2AX was blocked by the expression of antisense-AIM3 (As-p18) (see FIG. 9b). In addition, the inventors found that AIM3 increased the phosphorylation of ATM and its target proteins (p53 and chk2) through various tests (FIG. 9c and data not shown). These results suggest that AIM3 interacts directly with ATM/ATR to activate not only ATM/ATR but also ATM/ATR-regulated proteins.

Finally, in order to examine the functional association between AIM3 and ATM/ATR-mediated diseases, the present inventors examined the expression level of AIM3 in various cancer cell lines. The results indicated that the expression level of AIM3 was reduced in some cancer cell lines (see FIG. 10a). To have a clue to the possible cause for the results, the present inventors compared the DNA content for AIM3 gene using genomic PCR analysis. As a result, it was confirmed that some cancer cell lines appeared to contain less amount of DNA than other cells. This indicates that the cell lines have loss of one allele for AIM3 (see FIG. 10b). Furthermore, we examined the expression level of AIM3 in tissues isolated from 9 leukemia patients and, as a result, found that AIM3 was expressed at a low level in the tissues of three patients. In this case, the expression of p21, a p53 target gene, was also strongly suppressed (see FIG. 10c). The level of AIM3 in normal tissues and cancer tissues isolated from liver cancer patients was analyzed by RT-PCR. As a result, it was confirmed that the level of AIM3 in the cancer tissues was cancer-specifically reduced (see FIG. 10d). These results suggest that the low level expression of AIM3 is association with various cancer cell lines and the tissues of cancer patients at high frequency.

As described above, it was first found in the present invention that AIM3 is a tumor suppressor gene and particularly, a haploinsufficient tumor suppressor gene acting in signal transduction pathways including ATM/ATR and p53.

BRIEF DESCRIPTION OF THE DRAWINGS

FIG. 2c shows the results of analysis of the incidence of tumors at different ages (months) in wild-type mice (+/+) and AIM3 heterozygous mice (+/−).
White bar: the numbers of autopsied wild-type mice (+/+)
Gray bar: the numbers of autopsied AIM3 heterozygous mice (+/−)
Black section: the numbers of mice with tumors (tumor +)

FIG. 4c shows the results of RT-PCR analysis and Western blot analysis to examine changes in the expression level of AIM3 by treatment with adriamycin (Adr), at different time.
Bars represent the population of G1/G0 phase cells and numbers represent the percentage of G1/G0 phase cells

EV: HCT116 cells transfected with an empty vector containing no AIM3 gene AIM3: HCT116 cells transfected with an AIM3 expression vector

+/+: wild-type mice

+/−: AIM3 heterozygous mice

EV: HCT116 cells transfected with an empty vector containing no AIM3 gene

AIM3: HCT116 cells transfected with an AIM3 expression vector

Figure 6A:
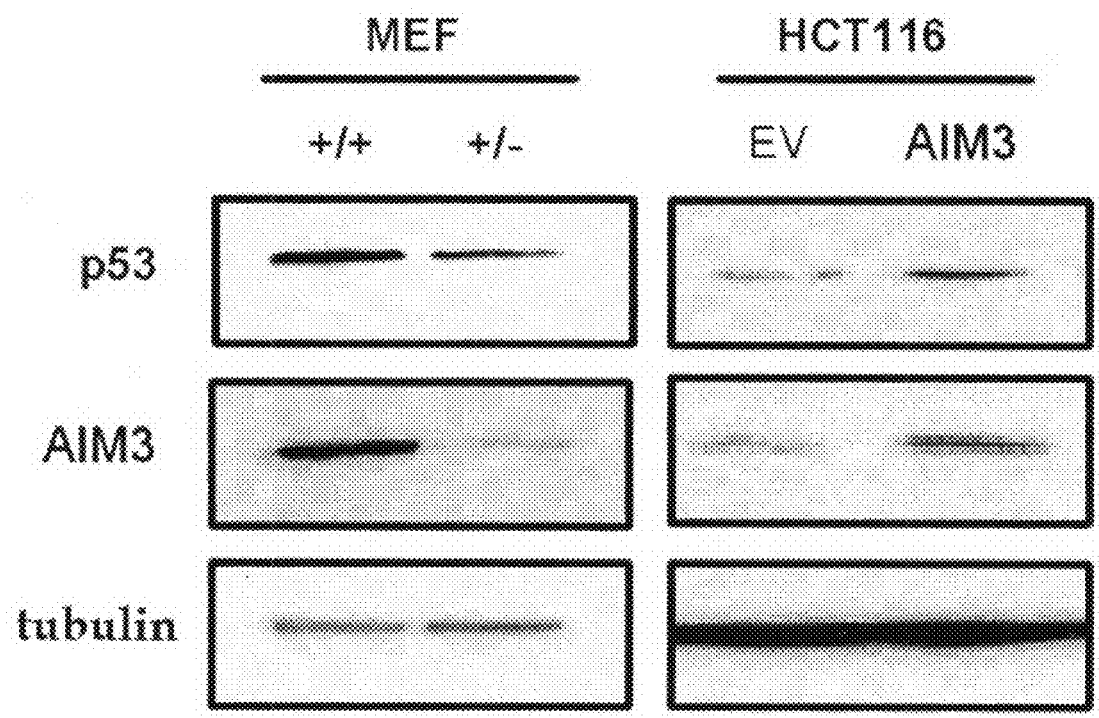
FIG. 6a shows the results of Western blot analysis to examine the effect of AIM3 on p53 expression in mouse embryonic fibroblasts (MEFs) derived from AIM3 heterozygous mice (+/−) and HCT116 cells transfected with an AIM3 expression vector.
Figure 6B:
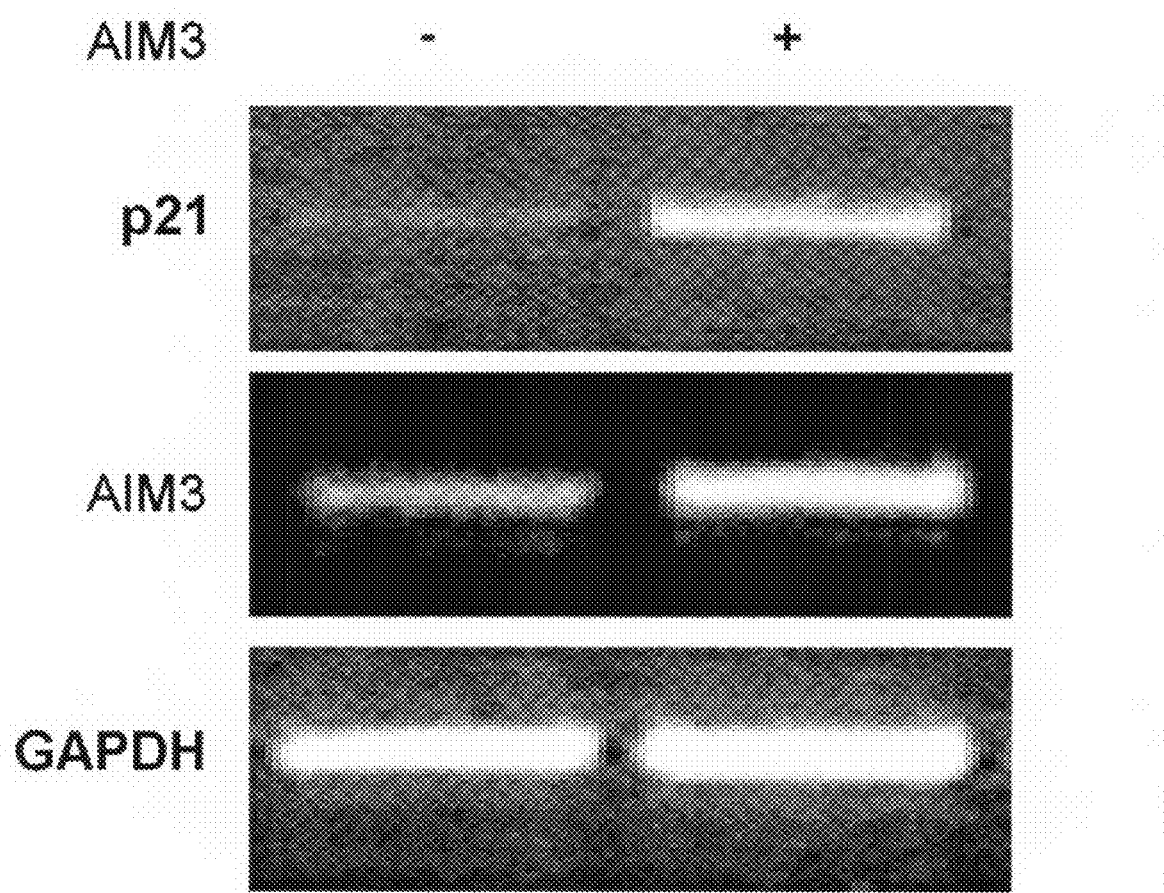

FIG. 6b shows the results of RT-PCR to examine the effect of AIM3 on the p53-dependent transcription of p21.

−: HCT116 cells transfected with an AIM3 expression vector

+: HCT116 cells transfected with an empty vactor containing no AIM3 gene

Figure 6C:
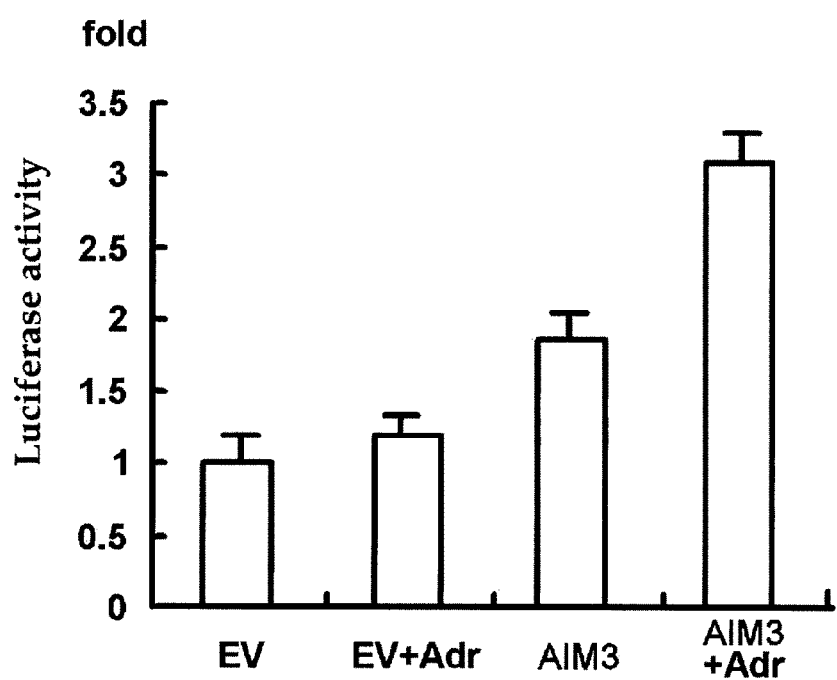

FIG. 6c shows the results of luciferase assay using a vector containing a p21 promoter-fused luciferase gene, to examine the effect of AIM3 on the p53-dependent transcription of p21.

Figure 6D:
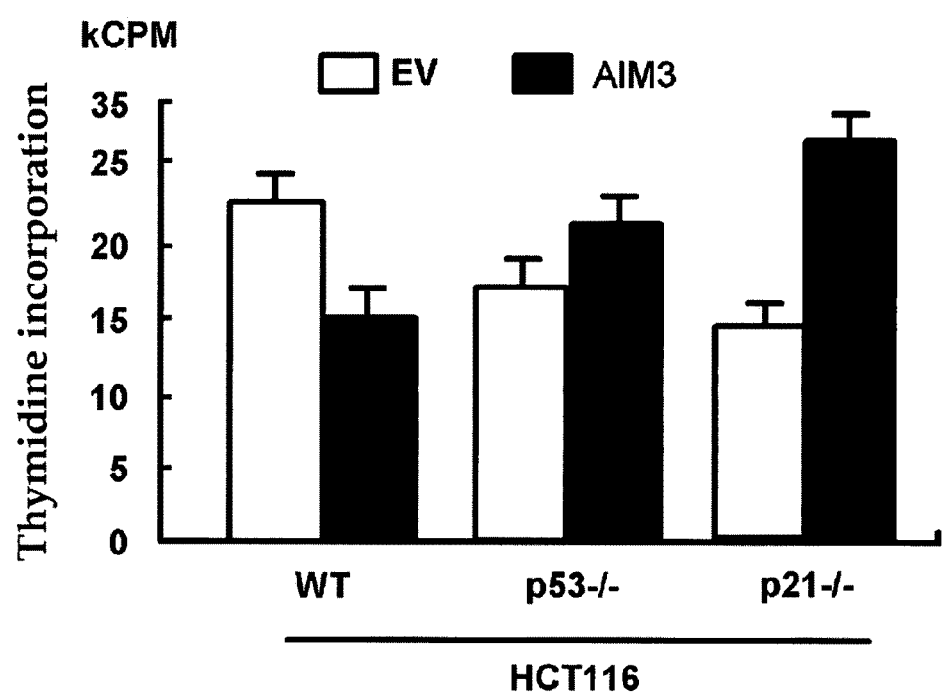

EV: HCT116 cells transfected with an empty vector containing no AIM3 were not treated with anything EV+Adr: HCT116 cells transfected with an empty vector containing no AIM3 were treated with adriamycin AIM3: HCT116 cells transfected with an AIM3 expression vector were not treated with anything AIM3+Adr: HCT116 cells transfected with an AIM3 expression vector were treated with adriamycin FIG. 6d illustrates the effect of ATM3 on the proliferation of wild-type HCT116 cells (WT), p53 gene-null HCT116 cells (p53−/−) and p21 gene-null HCT116 cells (p21−/−).

EV: HCT116 cells transfected with an empty vector containing no AIM3 gene

AIM3: HCT116 cells transfected with an AIM3 expression vector

Figure 6E:
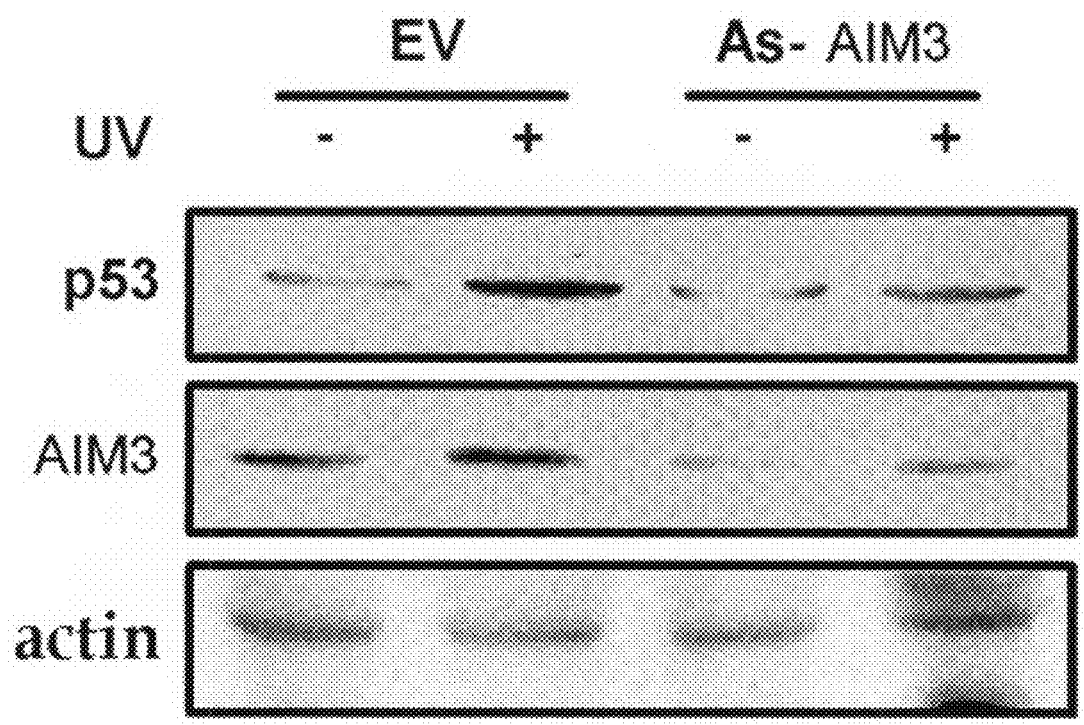
Figure 6E:
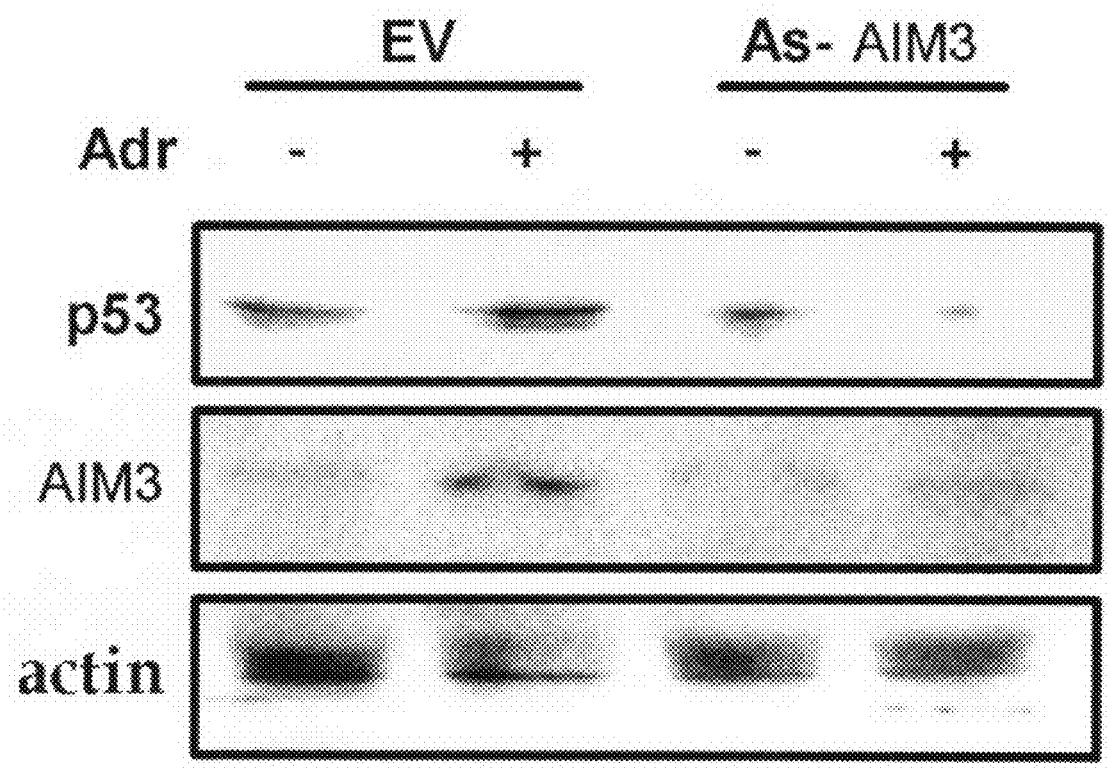

FIG. 6e shows the effect of AIM3 on p53 induction caused by exposure to UV and treatment with adriamycin (Adr).

EV: HCT116 cells transfected with an empty vector containing no antisense-AIM3 (As-AIM3)

As-AIM3: HCT116 cells transfected with a vector containing antisense-AIM3

Figure 7A:
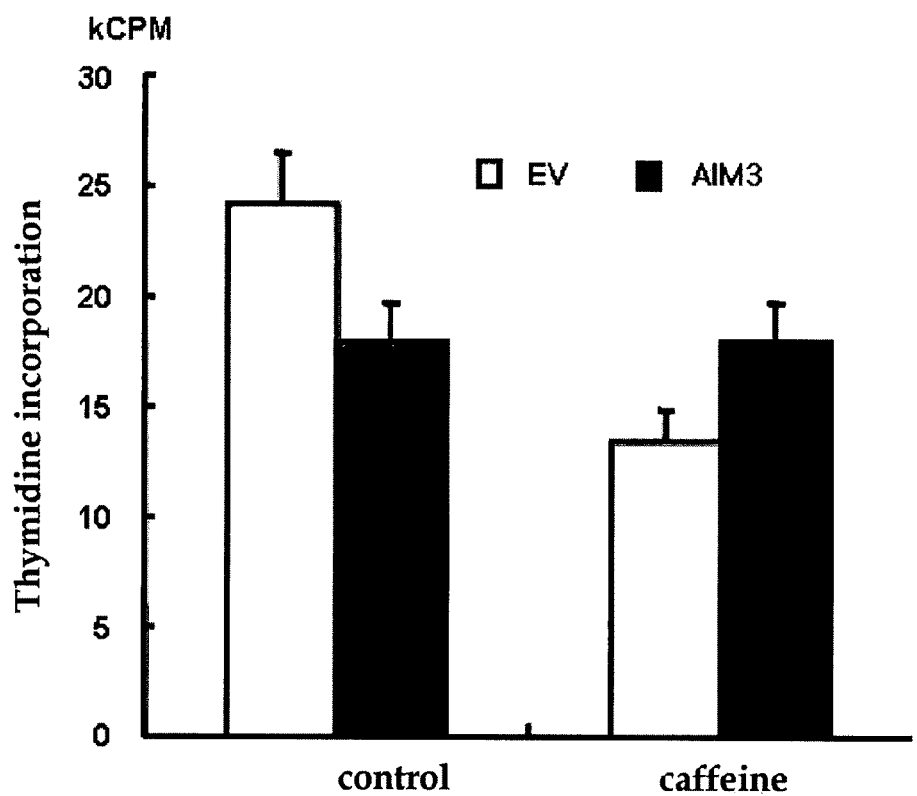

FIG. 7a illustrates the effect of caffeine on the anti-proliferation activity of AIM3.

EV: HCT116 cells transfected with an empty vector containing no AIM3 gene

AIM3: HCT116 cells transfected with an AIM3 expression vector

Figure 7B:
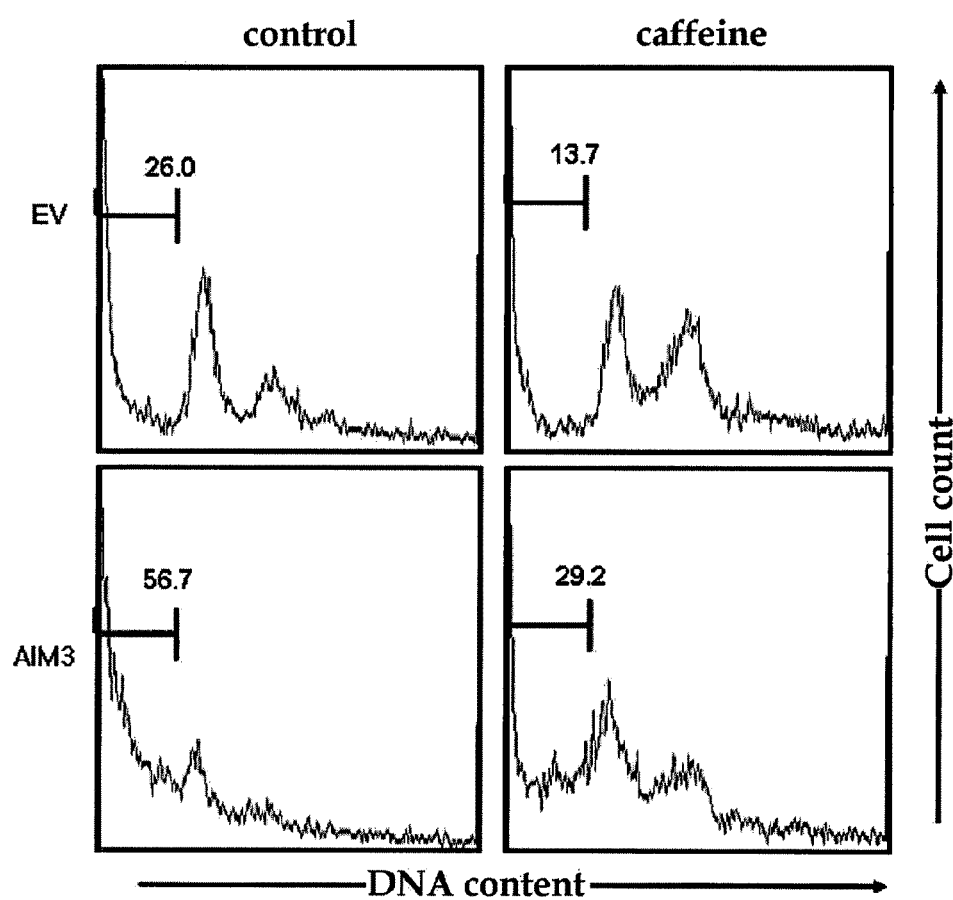

FIG. 7b shows the effect of caffeine on AIM3-induced apoptosis.

Figure 7C:
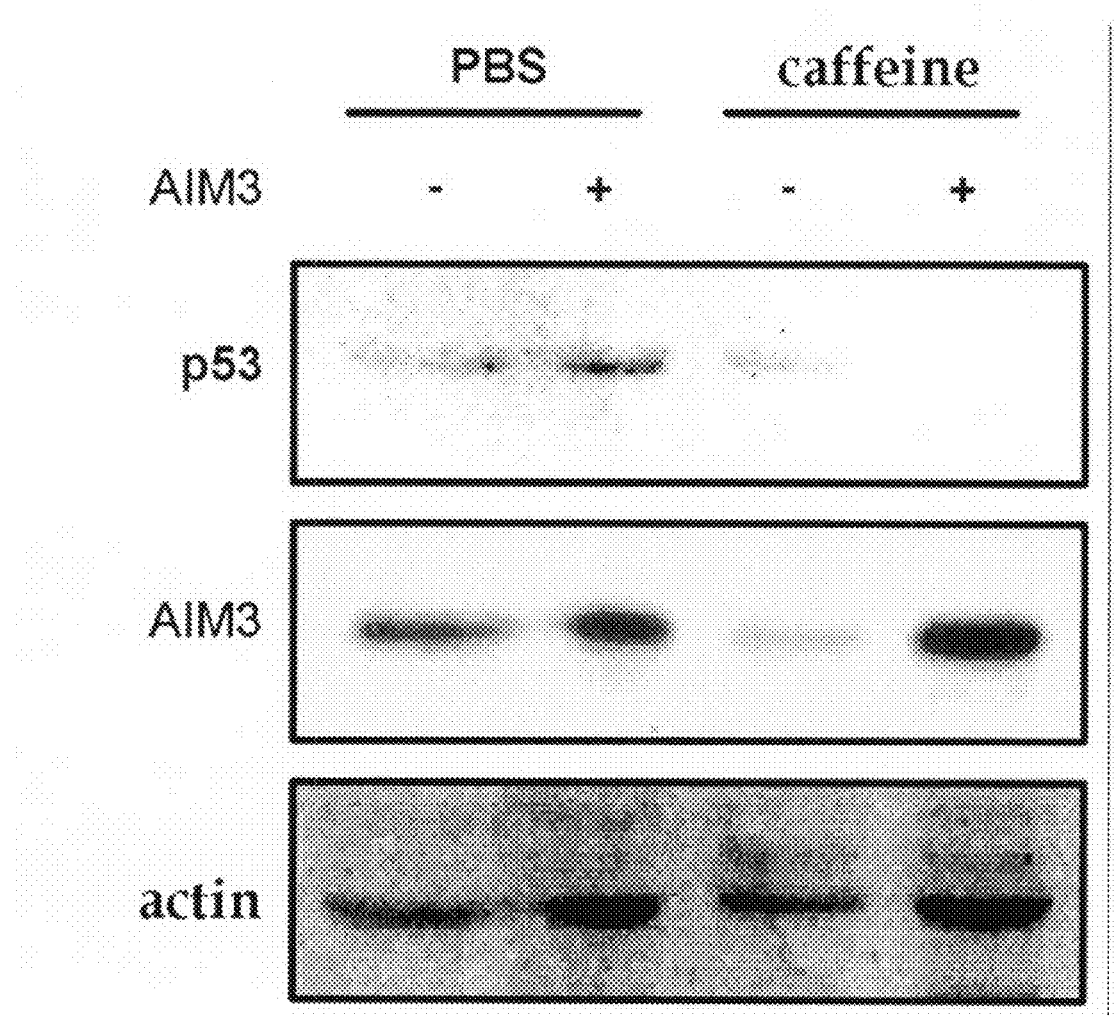

FIG. 7c shows the results of Western blot analysis to examine the effect of AIM3 on the induction of p53, after treatment with caffeine, an ATM inhibitor.

−: HCT116 cells transfected with an empty vector containing no AIM3 gene

+: HCT116 cells transfected with an AIM3 expression vector

Figure 7D:
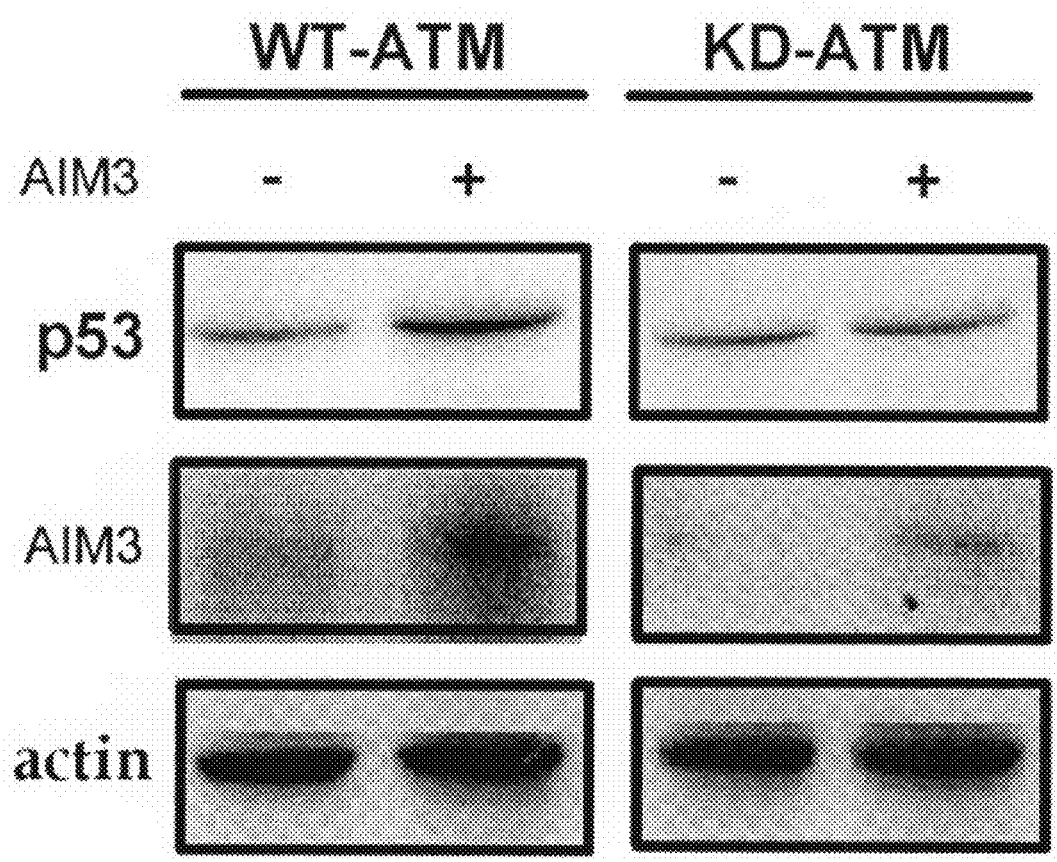

FIG. 7d shows the results of Western blot analysis to examine the effect of AIM3 on the induction of p53, after introducing a KD-ATM domain, a specific inhibitor of ATM activity, into cells.

−: HCT116 cells transfected with an empty vector containing no AIM3 gene

+: HCT116 cells transfected with an AIM3 expression vector

Figure 8A:
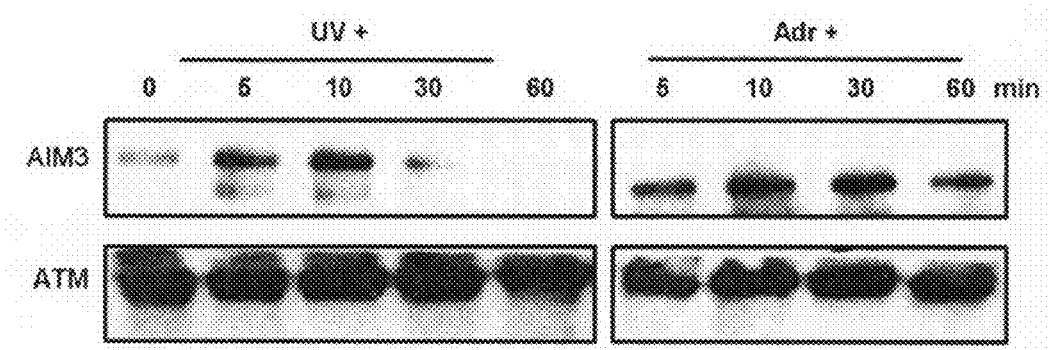

FIG. 8a shows the results of co-immunoprecipitation to determine the interaction between AIM3 and ATM, after treatment with UV and adriamycin.

Figure 8B:
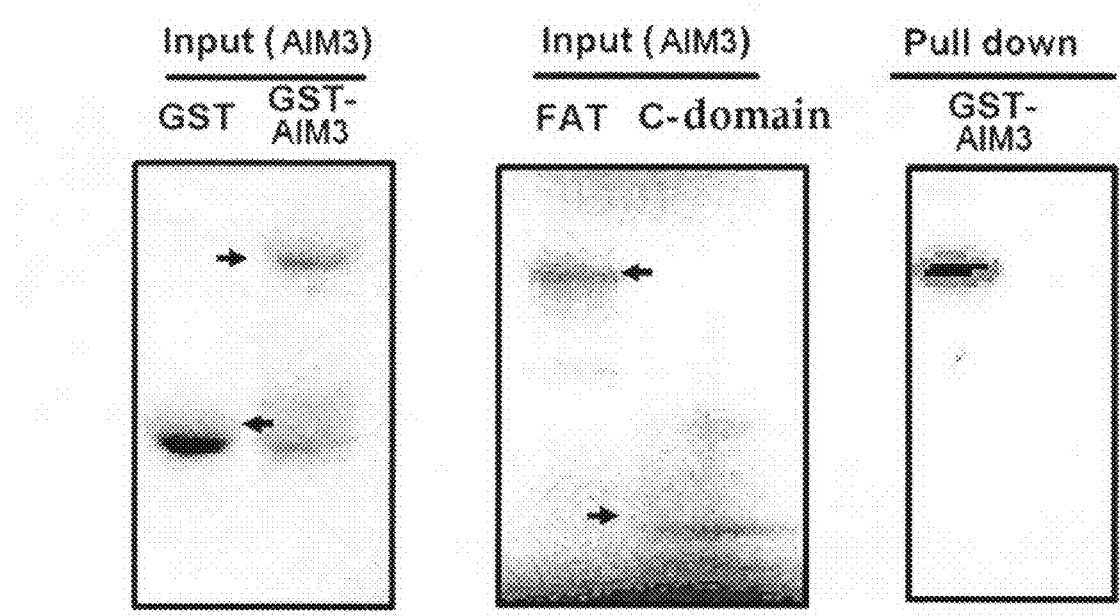

FIG. 8b shows the results of in vitro pull-down assay to determine the direct interaction between AIM3 and ATM.

Figure 8C:
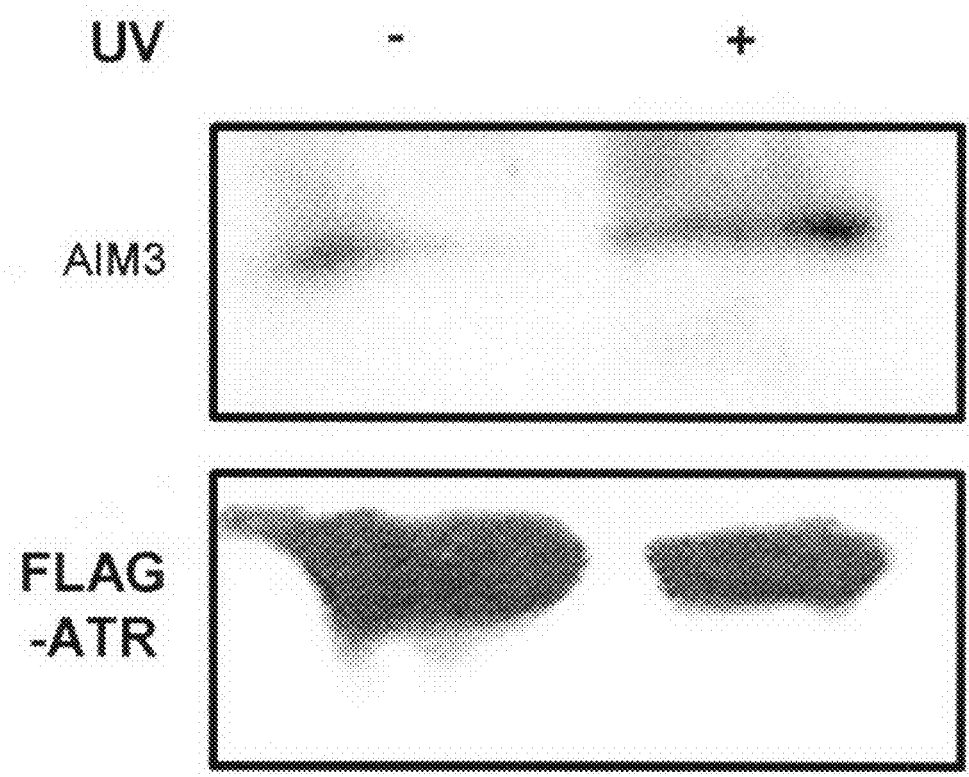

FIG. 8c shows the results of co-immunoprecipitation to determine the interaction between AIM3 and ATR, after exposure to UV.

Figure 9A:
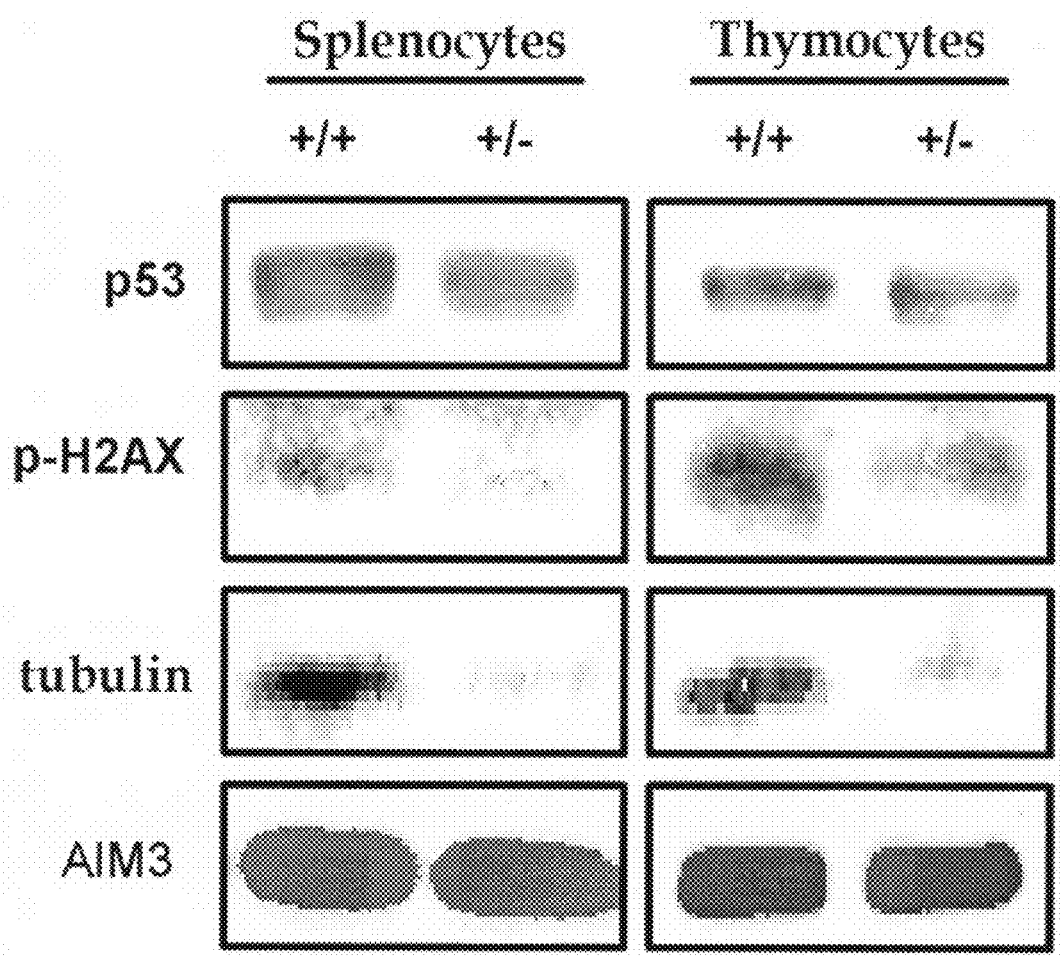

FIG. 9a shows the results of Western blot analysis to measure the phosphorylation level of H2AX, a substrate of ATM, in splenocytes and thymocytes isolated from wild-type mice (+/+) and AIM3 heterozygous mice (+/−).

p-H2AX: phosphorylated H2AX

Figure 9B:
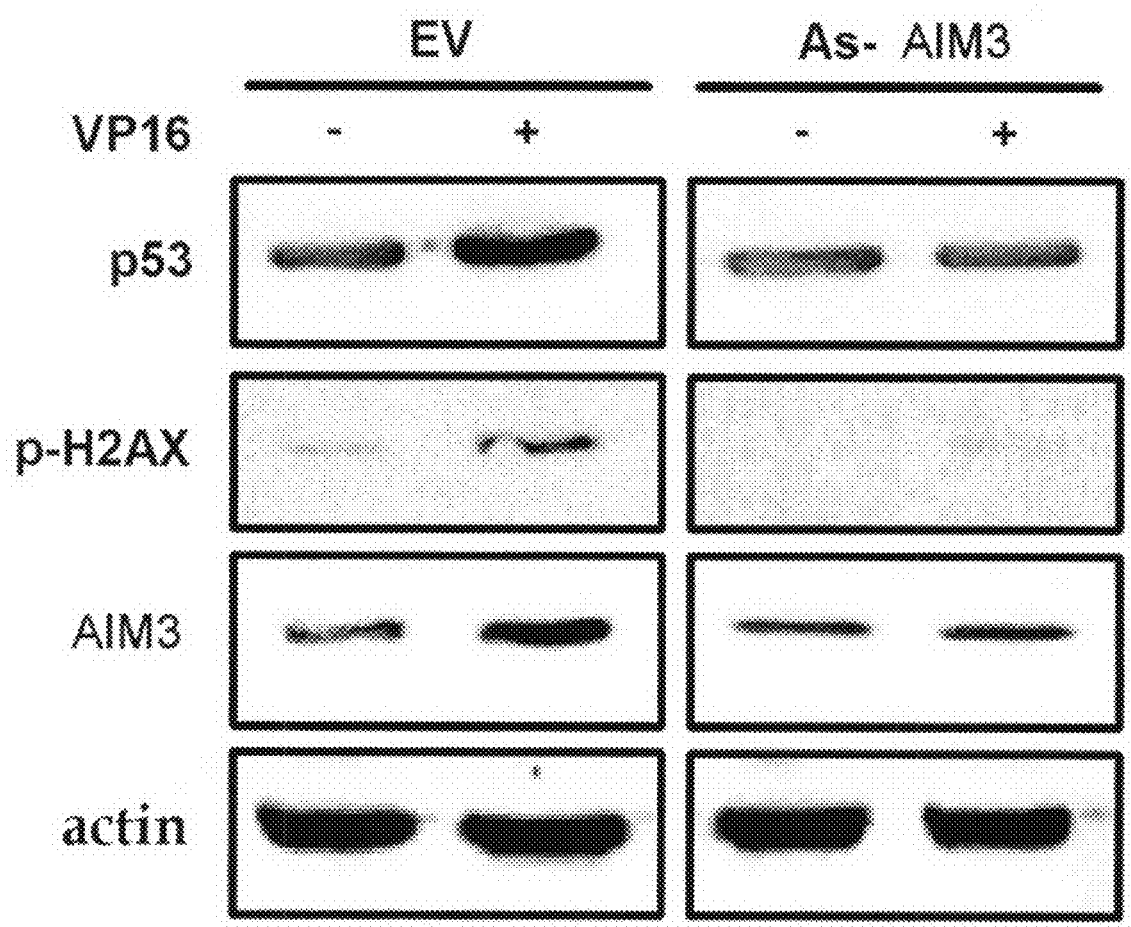

FIG. 9b shows the results of Western blot analysis to examine the effect of AIM3 on the phosphorylation of H2AX, a substrate of ATM, using antisense-AIM3 (As-AIM3).

−: no treatment with VP16, an apoptosis-inducer

+: treatment with VP16, an apoptosis-inducer

Figure 9C:
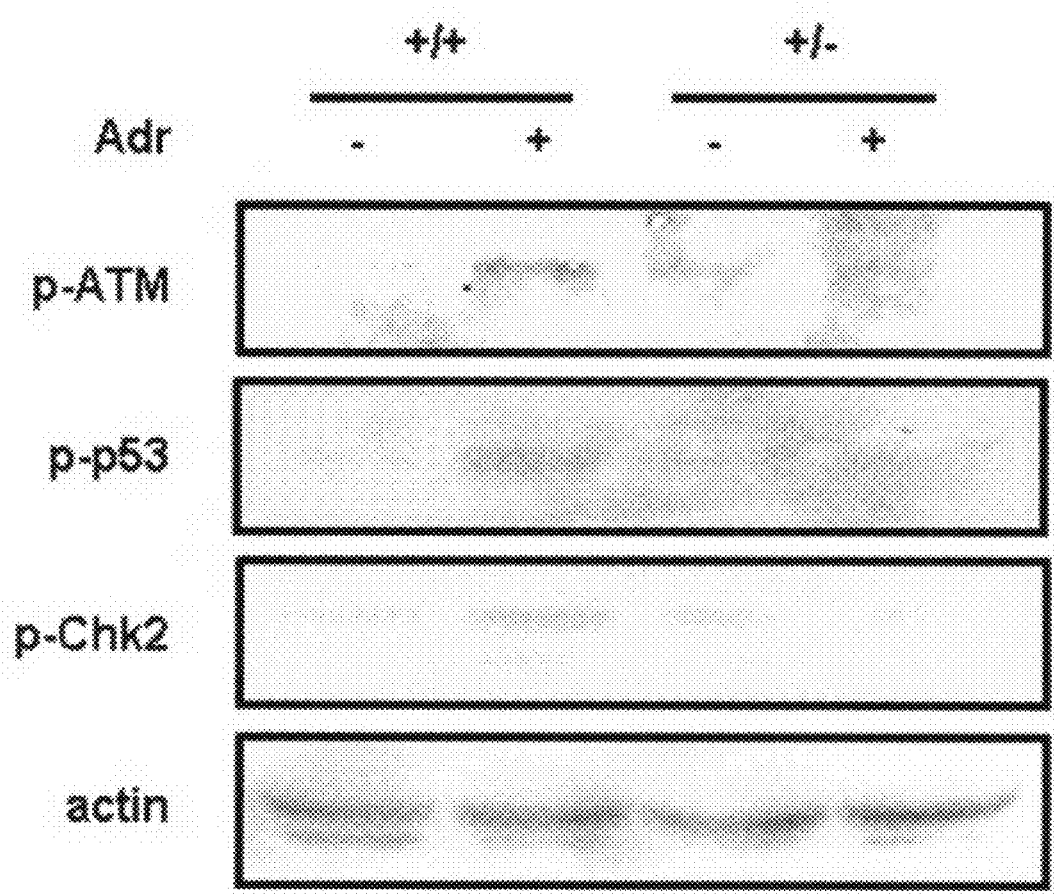

FIG. 9c shows the results of Western blot analysis to examine the effect of AIM3 on the phosphorylation of ATM and its target proteins (p53 and Chk2).

p-ATM: phosphorylated ATM p-p53: phosphorylated p53 p-Chk2: phosphorylated Chk2 actin: loading control

Figure 10A:
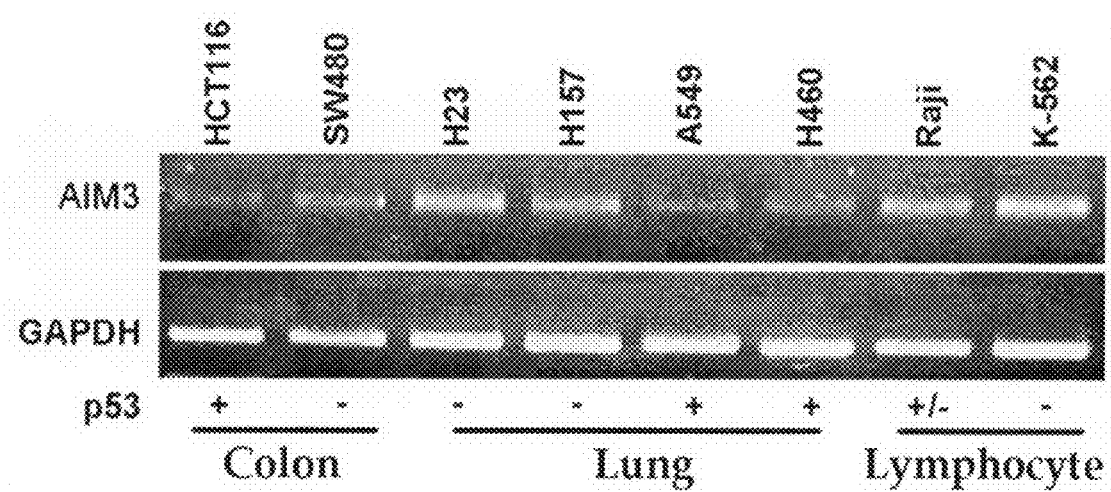

FIG. 10a shows the results of RT-PCR to measure the expression level of AIM3 in different human cancer cell lines.

Figure 10B:
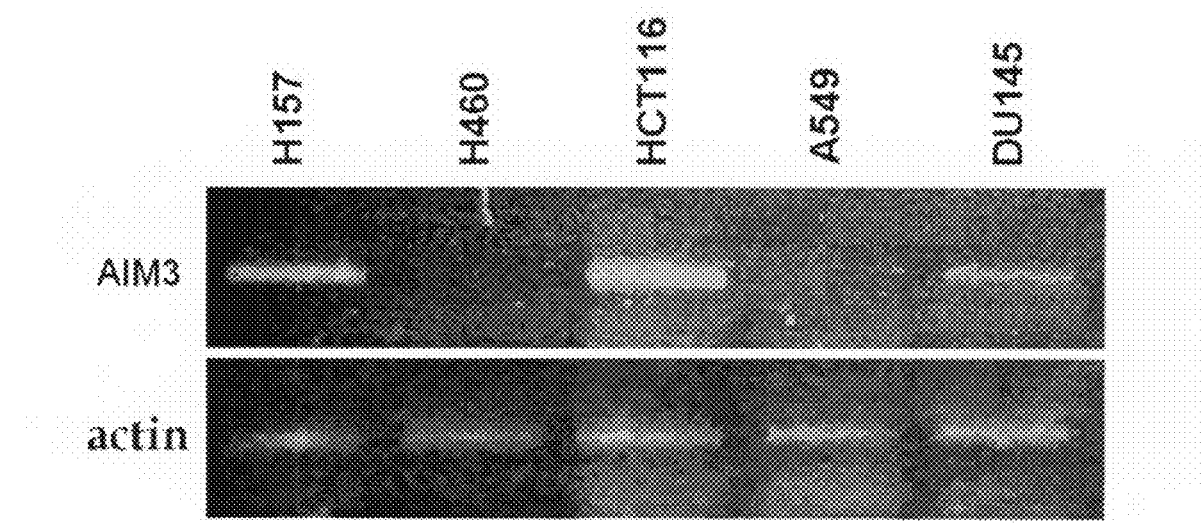

FIG. 10b shows the results of genomic PCR to examine the DNA content for AIM3 gene in different human cancer cell lines.

Figure 10C:
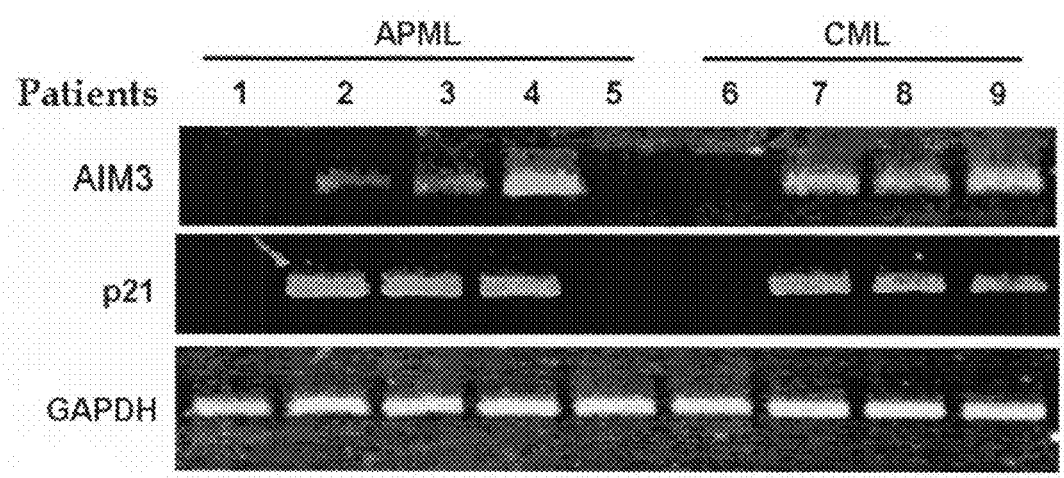

FIG. 10c shows the results of Western blot analysis to measure the expression level of AIM3 and p21 in tissues isolated from 9 leukemia patients.

APML: acute promyelocytic leukemia

CML: chronic myelocytic leukemia

Figure 10D:
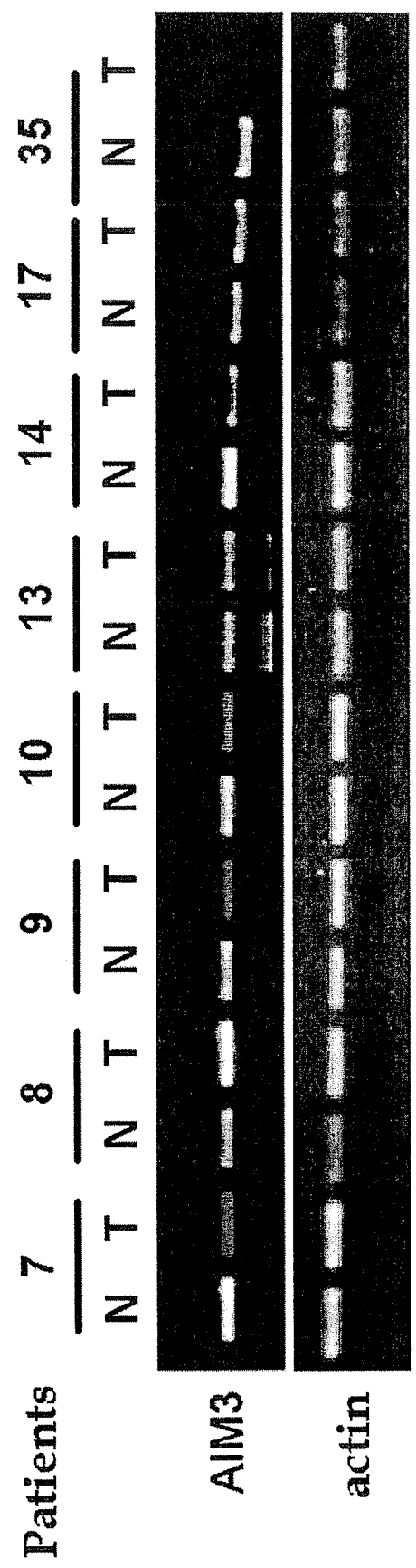

FIG. 10d shows the results of RT-PCR to measure the expression levels of AIM3 in normal tissues and cancer tissues isolated from 9 liver cancer patients.

N: normal tissues at tumor-adjacent sites

T: liver cancer tissues

BEST MODE FOR CARRYING OUT THE INVENTION

Hereinafter, the present invention will be described in detail by the following examples. It is to be understood, however, that these examples are given for illustrative purpose only and are not construed to limit the scope of the present invention.

EXAMPLE 1

Generation of AIM3 Gene-Deficient Mutant Mice

The present inventors generated AIM3-deficient mice by a gene trap method (Zambrowicz, B. P. et al., *Nature*, 392:608-611, 1998). Among the embryonic stem cell library of 129/SvEvBrd mouse in which the gene trap vector was randomly introduced (OmniBank Library, Lexicon Genetics), the OST377244 clone including AIM3 genes mutated by the integration of the gene trap vectors was found out. Using this clone, C57BL6/albino AIM3 heterozygous mice were generated following the standard protocol of Lexicon Genetics, Inc. The heterozygous mice were interbred to generate the homozygous offspring.

EXAMPLE 2

Figure 1A:
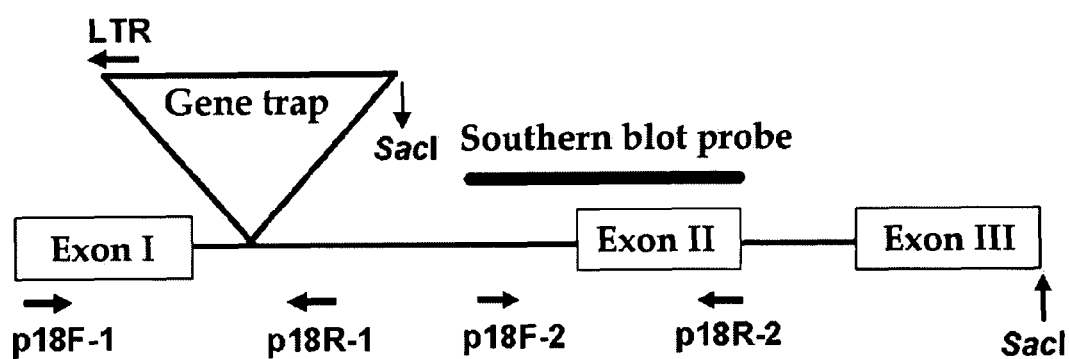
FIG. 1a is a schematic representation of a gene trap vector inserted into an AIM3 gene.

Examination of Genotypic and Phenotypic Characteristics of AIM3 Gene-deficient Mice <2-1> Determination of Site of Gene Trap Vector Insertion in AIM3 Allele The site of a gene trap vector insertion in an AIM3 mutant allele was determined by sequencing analysis. Here, the sequencing was performed by Pangenomics, a sequencing company. As shown in FIG. 1a, the sequencing results indicated that the gene trap vector was inserted between exon I and exon II of the AIM3 gene.

<2-2> Genomic PCR Analysis

From the tail of each of the mice generated in <Example 1>, genomic DNA was isolated. Then, about 1.5-kb DNA fragment containing the exon I region of the AIM3 gene was amplified by PCR with a primer pair of p18F-1 and p18R-1 (SEQ ID NO: 3 and SEQ ID NO: 4) (see FIG. 1a). In addition, about 0.8-kb DNA fragment containing a part of the AIM3 gene and a part of the gene trap vector was amplified by PCR with the p18F-1 primer and an LTR primer (SEQ ID NO: 5) binding to the gene trap vector (about 5.7 kb) integrated into the genome (see FIG. 1a). The PCR reaction consisted of the following: denaturation of template DNA at 94° C. for 5 min; and then, 30 cycles of 1 min at 94° C., 1 min at 54° C., and 2 min at 72° C.

Figure 1B:
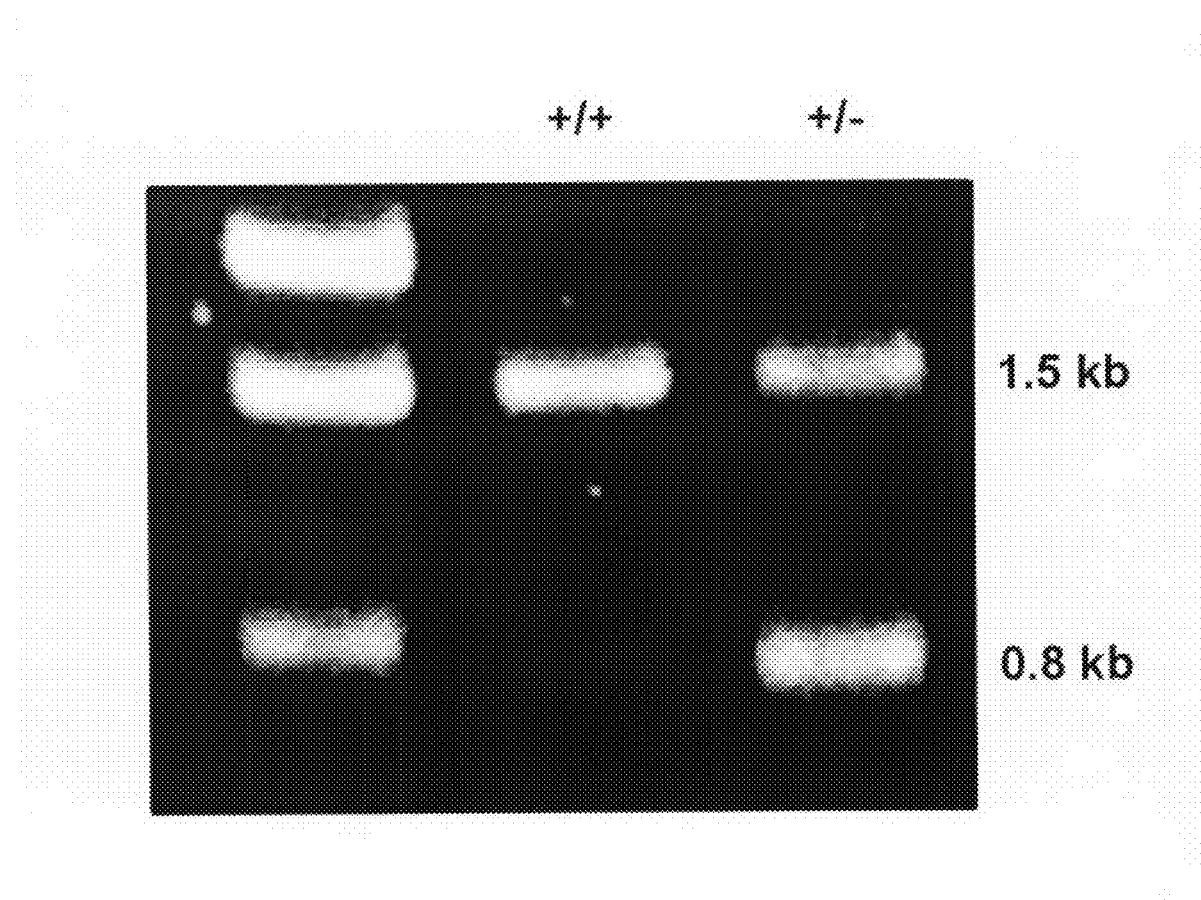
FIG. 1b shows the results of genomic PCR analysis to determine the insertion of a gene trap vector.
M: molecular weight marker
+/+: wild-type mice
+/−: AIM3 heterozygous mice

Interestingly, all of the generated mutant mice were heterozygote (AIM3$^{+/-}$ mice) producing both of 1.5 and 0.8 kb DNA fragments (see FIG. 1b). On the other hand, in the case of wild-type mice (AIM3$^{+/+}$ mice), only the 1.5-kb band could be found.

<2-3> Southern Blot Analysis

From the tail of each mouse, genomic DNA was isolated and digested with SacI, followed by gel electrophoresis to separate the digested DNA fragments. Then, a PCR product amplified with p18F-2 and p18R-2 primers shown in SEQ ID NO: 6 and SEQ ID NO: 7, which contains the exon II region of the AIM3 gene, was labeled with a radioactive isotope (see FIG. 1), and the labeled probe was hybridized with the digested DNA fragments (southern, E. M., *J. Mol. Biol.*, 98:503, 1975).

Figure 1C:
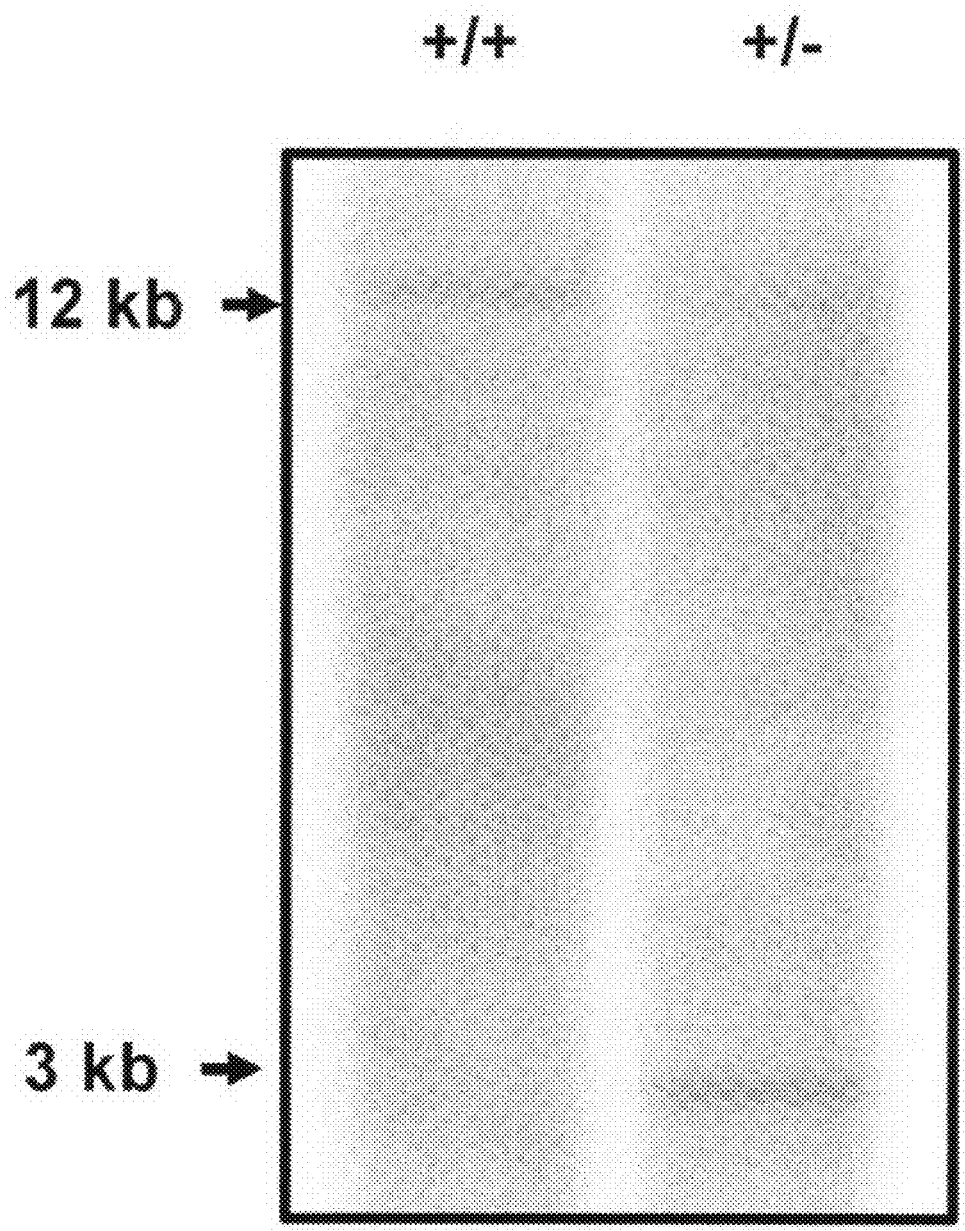
FIG. 1c shows the results of Southern blot analysis to determine the insertion of a gene trap vector.
+/+: wild-type mice
+/−: AIM3 heterozygous mice

As shown in FIG. 1c, a band of about 12 kb was detected in wild-type mice but additional band of about 3 kb was detected in the heterozygous mice.

<2-4> Determination of Induction of Embryonic Lethality Caused by AIM3 Gene Deletion In the analysis in Examples <2-2> and <2-3>, offspring with a homozygous genotype could not be found. Thus, in order to examine whether the deficiency of the AIM3 gene induces embryonic lethality, the genotype of post-natal mice and the genotype of embryos on different time after fertilization were examined by genomic PCR according to the same method as in Example <2-2>. The results are shown in Tables 1 and 2 below.

As shown in Table 1, among a total of 262 survival mice, 114 mice were wild type (+/+) and 148 mice were heterozygous (+/−). None of surviving mice was homozygous (−/−). Particularly, the heterozygous mice were born at a similar ratio with the wild-type littermates, indicating that about 50% of the heterozygous mice would die during the pre-natal stage. As shown in Table 2, among total of 38 embryos isolated at 7.5-9.5 days after fertilization, only one embryo at 8.5 days containing the homozygous genotype was detected. This indicates that the AIM3 homozygous mice would be early embryonic lethal.

TABLE 1

Post-natal segregation ratio of genotype from the offspring generated by the intercrosses between the C57BL6 AIM3 heterozygous mice

|  | Total | +/+ | +/− | −/− |
|---|---|---|---|---|
| Number of surving mice | 262 | 114 | 148 | 0 |
| % | 100 | 43.5 | 56.5 | 0 |

TABLE 2

Embryonic segregation ratio of genotype from the offspring generated by the intercrosses between the C57BL6 AIM3 heterozygous mice

| Day of Gestation | Total | +/+ | +/− | −/− | Resorbed |
|---|---|---|---|---|---|
| 7.5 days | 28 | 7 | 15 | 0 | 6 |
| 8.5 days | 34 | 11 | 16 | 1 | 6 |
| 9.5 days | 21 | 8 | 8 | 0 | 5 |
| Total | 83 | 26 | 39 | 1 | 17 |
| % |  | 31.3 | 47.0 | 1.2 | 20.5 |

The results suggest that loss of AIM genes leads to embryonic lethality.

<2-5> Western Blot Analysis

According to the method described in Ziak, M, et al. (Ziak, M, et al., *Biochem. Biophys. Res. Commun.* 280:363-367, 2001), proteins were isolated from various organs, such as small intestines, kidneys, heart and spleen. Then, according to the method described in Park S. G., et al. (Park S. G., et al., *J. Biological Chemistry* 274:16673-16676, 1999), Western blot analysis was performed using a polyclonal rabbit anti-AIM3 antibody. The anti-AIM3 antibody was prepared according to the method described in Kim, T. et al. (Kim, T. et al., *J. Biol. Chem.*, 275:21768-21772, 2000).

Figure 1D:
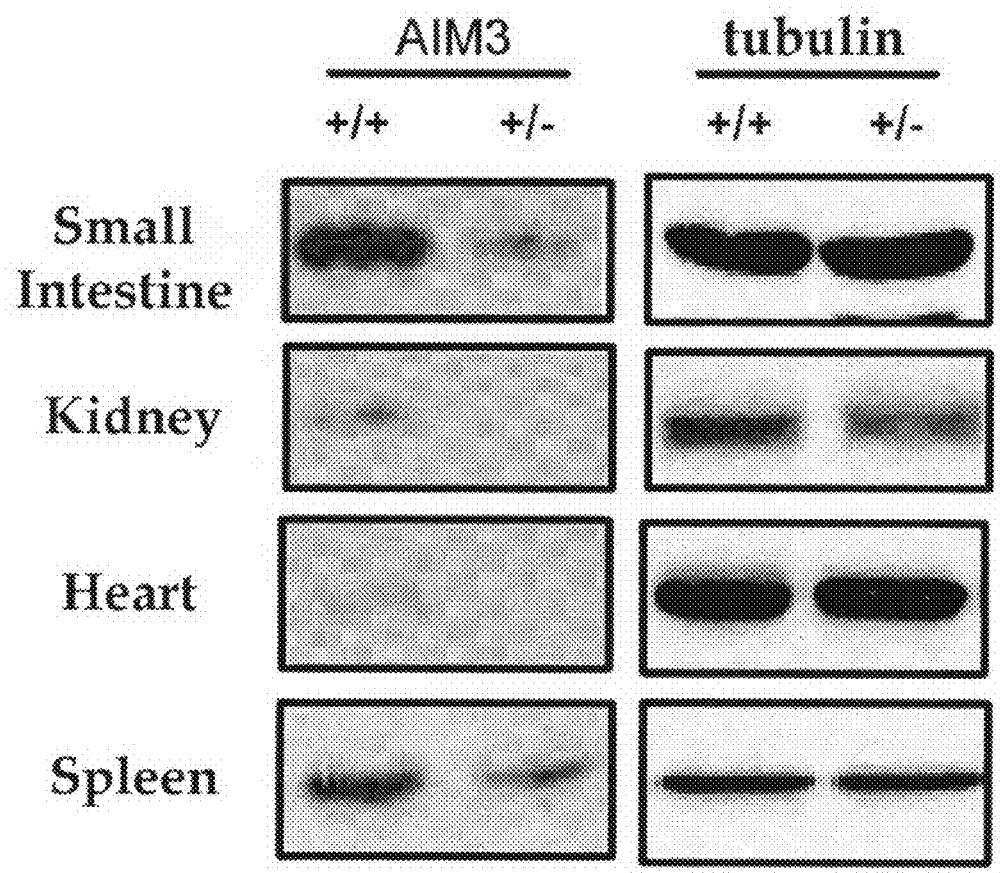
FIG. 1d shows the results of Western blot analysis to determine the expression level of AIM3 in various organs of wild-type mice (+/+) and AIM3 heterozygous mice

As shown in FIG. 1d, although the degree of reduction varied depending on the organs, the expression level of AIM3 in the organs of the AIM3$^{+/-}$ mice was significantly lower than that in the organs of wild-type mice.

EXAMPLE 3

Examination of histological characteristics of AIM3$^{+/-}$ mice

In order to determine the functions of the AIM3 gene, the present inventors isolated tissues and organs from the AIM3$^{+/-}$ mice and analyzed the histological characteristics of the isolated tissues and organs.

At first, after sacrificing mice at given time intervals, various tissues were isolated and fixed with 10% formalin. The fixed tissues were embedded in paraffin, followed by subjecting into H&E staining. In order to determine B cell metastasis, immunohistochemical staining for surface marker B220 was performed with paraffin slide. After de-paraffin using xylene, the slide was incubated in a blocking buffer (1:100, 5% BSA and 0.1% Tween 20/PBS) containing an anti-B220 antibody (Santacruz Biotech.) for 2 hours. After the slide was washed with PBS, the tissues fixed to the slide were incubated again with an avidin-conjugated secondary antibody and DAB solution.

Figure 2A:
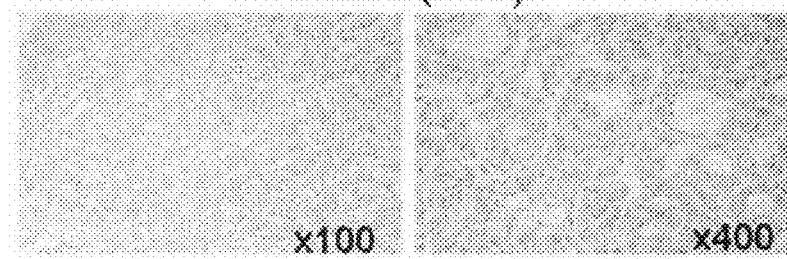
FIG. 2a shows the results of immunohistochemical staining of various tissues and organs isolated from AIM3 heterozygous mice.
Figure 2A:
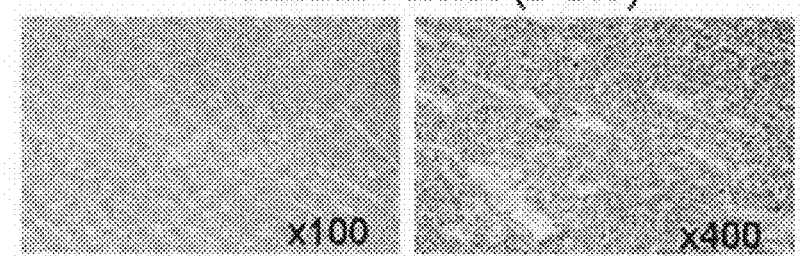
Figure 2A:
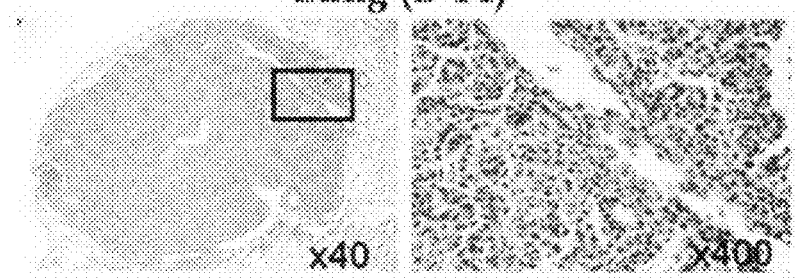
Figure 2A:
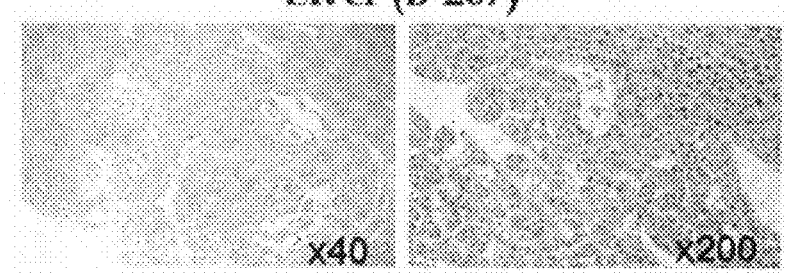
Figure 2A:
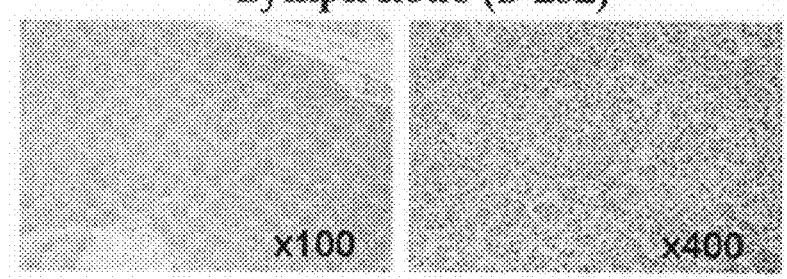

As a result, various tumors were found in the AIM3$^{+/-}$ mice (see Table 3 and FIG. 2a). Interestingly, among 18 tumor-developing AIM3$^{+/-}$ mice, 14 mice contained lymphoma which originated from the spleen or lymph node, and 5 mice had complex tumors. Specifically, adenocarcinoma was found in the breasts of 15-month-old AIM3$^{+/-}$ mice (B-63) and 23-month-old AIM3$^{+/-}$ mice (B-95), adenocarcinoma in the seminal vesicles of 19-month-old AIM3$^{+/-}$ mice (B-103), and hepatocarcinoma and sarcoma of unknown origin in 22-month-old AIM3$^{+/-}$ mice (B-207). All of these cancers showed the typical malignant phenotypes, such as anaplasia and invasiveness. Furthermore, lymphoma was found in the lymph nodes of 22-month-old AIM3$^{+/-}$ mice (B-232) and well-differentiated carcinoma which originated from the bronchiole epithelium was observed in 17-month-old AIM3$^{+/-}$ mice (B-14).

Figure 2B:
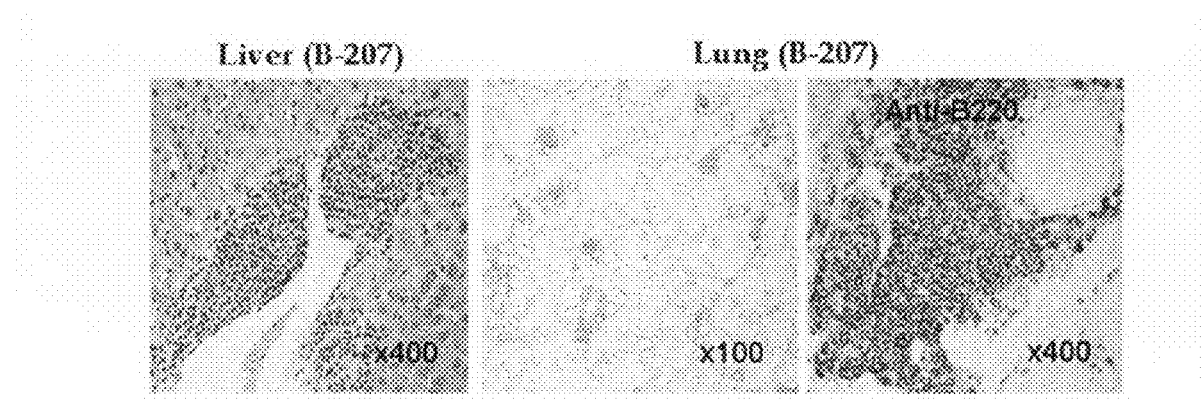
FIG. 2b illustrates the results using an anti-B220 monoclonal antibody, which shows that lymphoma cells metastasized into liver and lung.

It was found that some of lymphomas metastasized into other organs, such as the liver, kidneys, lungs and salivary glands (see FIG. 2b). The incidence of these tumors was remarkably increased after 15 month-old (see FIG. 2c and Table 3).

TABLE 3

Tumors found in AIM3$^{+/-}$ mice

| | Mouse ID | Tumor locus | Metastasis | Age (month) |
|---|---|---|---|---|
| Single solid tumor | B-2 | Liver, dysplasia | —* | 8 |
| | B-268 | Liver | — | 23 |
| | B-63 | Breast (adenocarcinoma) | — | 15 |
| | B-233 | Seminal vesicle (adenocarcinoma) | — | 21 |
| Lymphoma | B-191 | Spleen | Salivary gland, kidneys, lungs | 25 |
| | B-262 | Spleen | Lungs | 20 |
| | B-275 | Mesenteric lymph node | Liver, spleen | 17 |
| | B-148 | Spleen | — | 24 |
| | B-264 | Spleen | Salivary gland | 15 |
| | B-143 | Cervical lymph node | Liver, lungs | 25 |
| | B-226 | Spleen | Lungs | 22 |
| | B-261 | Spleen | Lungs | 20 |
| | B-321 | Spleen | Liver | 1 |
| Multiple tumor | B-103 | Seminal vesicle (adenocarcinoma), metastatic lymphoma | Spleen, kidneys | 19 |
| | B-14 | Lung adenocarcinoma, metastatic lymphoma | Salivary gland | 17 |
| | B-95 | Breast adenocarcinoma (solid tumor), metastatic lymphoma | Salivary gland, spleen | 23 |
| | B-232 | Lung adenocarcinoma (solid tumor), lymphoma (lymph node) | — | 22 |
| | B-207 | Metastatic sarcoma (liver), hepatic carconoma (liver), metastatic lymphoma | Spleen, liver, lungs, salivary gland | 22 |

*negative

As shown in the above results, all of various tumors spontaneously formed in the AIM3-deficient heterozygous mice led us to suspect that AIM3 is a strong tumor suppressor involved in general tumorigenic mechanisms.

EXAMPLE 4

Identification of Relation Between Cell Cycle and AIM3

A rapid cell cycle is a typical indicatin for tumorigenesis (Evan and Vousden, Nature, 411:342-348, 2001). Accordingly, it was addressed whether AIM3 could play a role in cell cycle control.

<4-1> Examination of Change of Cell Cycle in AIM3$^{+/-}$ Mouse-derived Cells

Figure 3A:
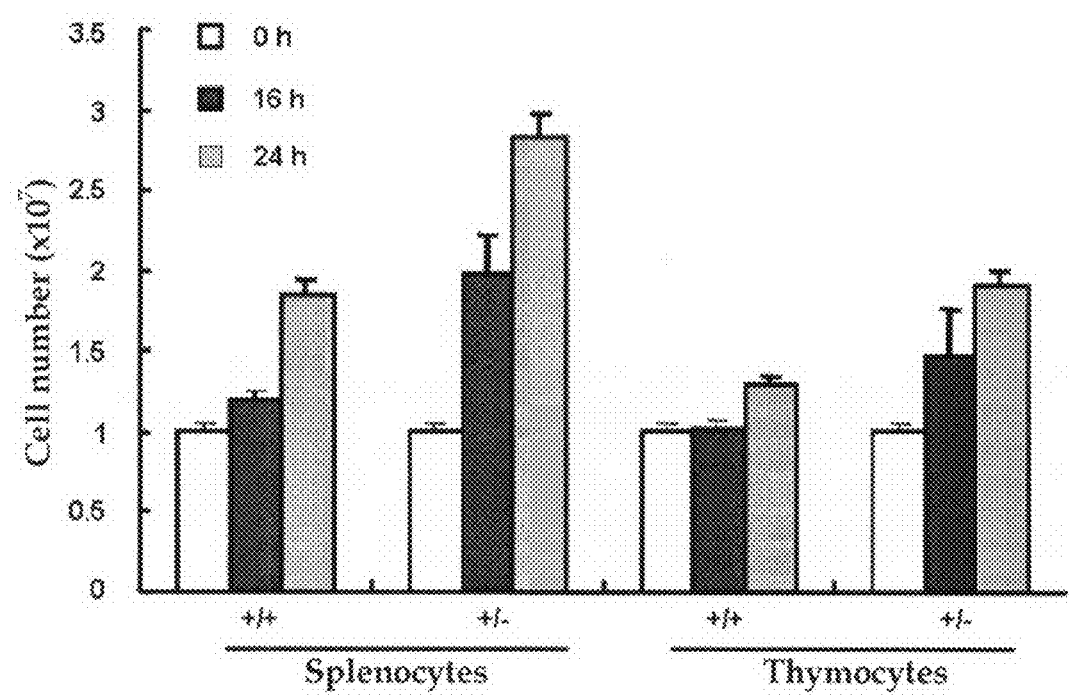
FIG. 3a shows the results of cell counting to measure the proliferation rate of the splenocytes and thymocytes isolated from wild-type mice (+/+) and AIM3 heterozygous (+/−).

First, the present inventors examined the cell proliferation rate of AIM3$^{+/-}$ mouse-derived cells, compared to that of wild-type mouse cells. For this purpose, from 4-week-old wild-type mice and AIM3$^{+/-}$ mice, the splenocytes and thymocytes were isolated, and the number of cell according to culture time was counted. As shown in FIG. 3a, the results showed that the AIM3$^{+/-}$ mice-derived cells proliferated faster than wild type mice cells.

Figure 3B:
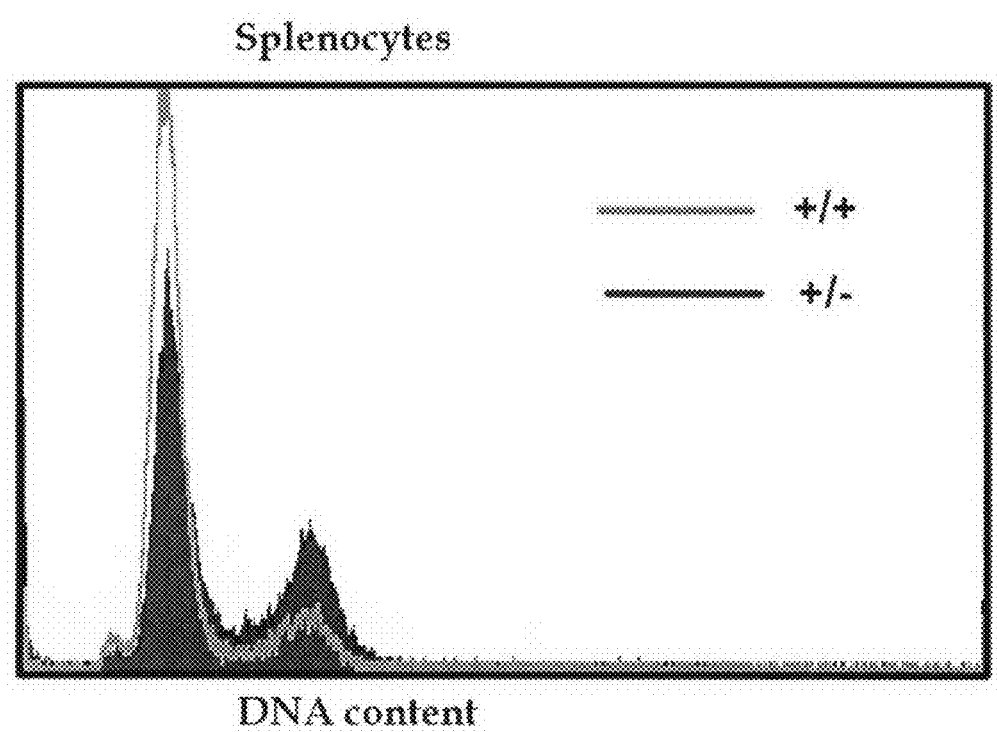
FIG. 3b shows the results of analysis of the cell cycle of splenocytes isolated from wild-type mice (+/+) and AIM3 heterozygous mice (+/−).

Then, in order to examine the cell cycle of the AIM3$^{+/-}$ mice-derived cells, FACS analysis was performed. The splenocytes isolated from 4-week-old wild-type mice and AIM3$^{+/-}$ mice were incubated overnight. The incubated cells were fixed with 1% PFA (paraformaldehyde) and stained with PI (propidium iodide). FACS analysis was conducted on 20,000 cells per sample. As shown in FIG. 3b, the splenocytes isolated from the AIM3$^{+/-}$ mice showed faster cell cycle than the wild-type mice cells.

Figure 3C:
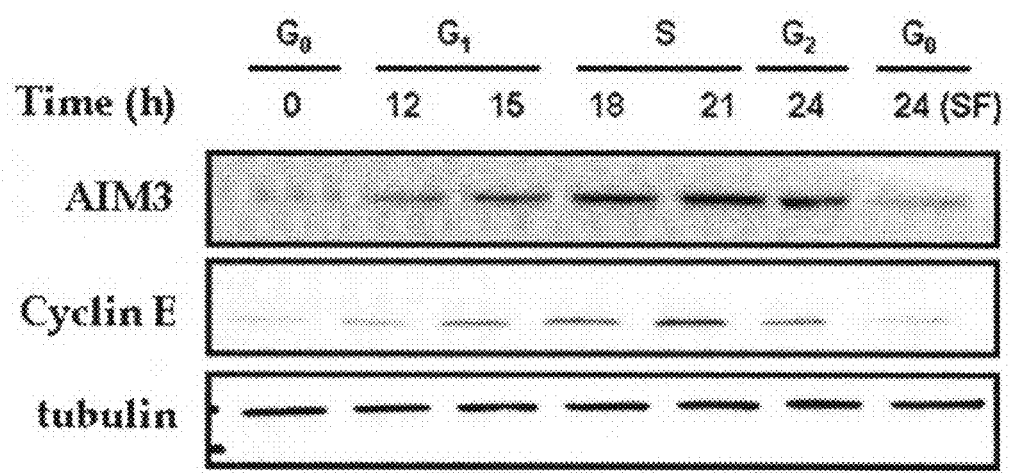
FIG. 3c shows the results of Western blot analysis to determine the expression level of AIM3 in each phase of the cell cycle.

<4-2> Examination of Change in Expression Level of AIM3 with Change in Cell Cycle In order to determine the functions of AIM3 during the cell cycle, it was examined whether AIM3 is expressed depending on the cell cycle. HCT116 cells incubated in a serum-free medium for 24 hours and then incubated them again in a serum-containing medium to synchronize cell cycle. The expression level of AIM3 of the synchronized cells in different time under serum-deprivation and serum-re-fed conditions was measured by Western blot analysis. As a result, the AIM3 was remarkably induced during the DNA synthetic phase (see FIG. 3c).

Figure 3D:
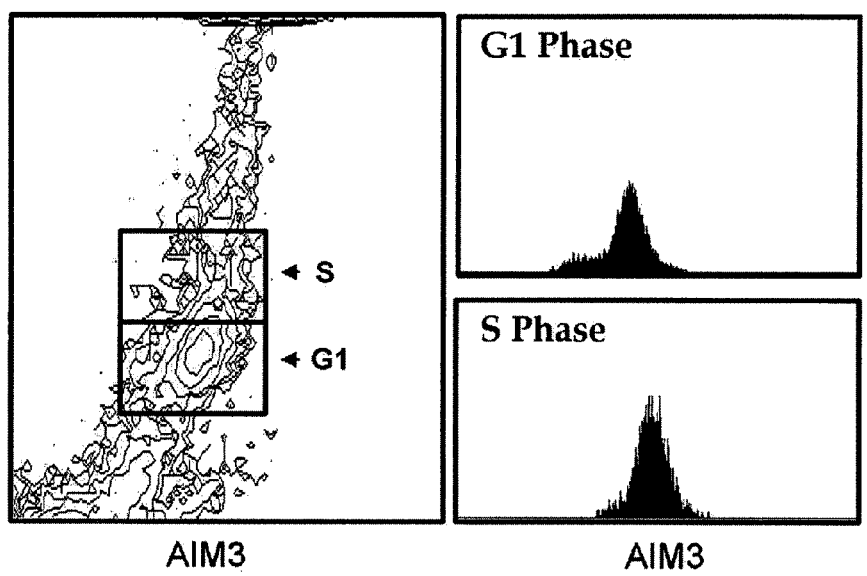
FIG. 3d shows the results of FACS analysis to determine the expression level of AIM3 at different cell cycle.
Left panel: DNA content (Y-axis) and the expression of AIM3 (X-axis) are analyzed by FACS and the density of cell is illustrated in contour lines. The "S" portion represents cells in the DNA synthetic phase on the basis of DNA content, and the "G1" portion represents cells in the G1/G0 phase.
Right panel: the expression level of AIM3 in "G1" and "S" portion respectively in the left panel is shown in histograms. The X-axis represents the expression level of AIM3, and the Y-axis represents cell number.

In order to confirm this fact further, the present inventors performed FACS analysis. HCT116 cells (Human colon adenocarcinoma cell line) were fixed with 1% PFA and neutralized, and were cultured with an anti-AIM3 monoclonal antibody. Then, the cells were cultured with a FITC-conjugated anti-mouse goat IgG antibody (Pierce). And then, the cells were co-stained with PI, followed by FACS analysis. As a result, AIM3 was remarkably induced in the DNA synthetic phase (see FIG. 3d). This coincides with the result of Western blot analysis. All of these results indicate that AIM3 is induced in the DNA synthetic phase.

<4-3> Examination of Cellular Localization of AIM3 Caused by Cell Proliferation

In order to understand the functional reason of AIM3 induction during the DNA synthetic phase, the present inventors investigated the cellular localization of AIM3 in cell growth arrest and cell proliferation conditions. For this purpose, DU145 cells (prostate cancer cell line) were cultured in each of a 10% serum-containing RPMI-1640 medium (complete media (CM)) and a serum-free media (SF), fixed with 100% Me-OH and reacted with an anti-AIM3 monoclonal antibody. Then, they were reacted with anti-mouse goat IgG-FITC (Pierce), and stained with PI. The cellular localization of AIM3 was examined under a fluorescence microscope.

Figure 3E:
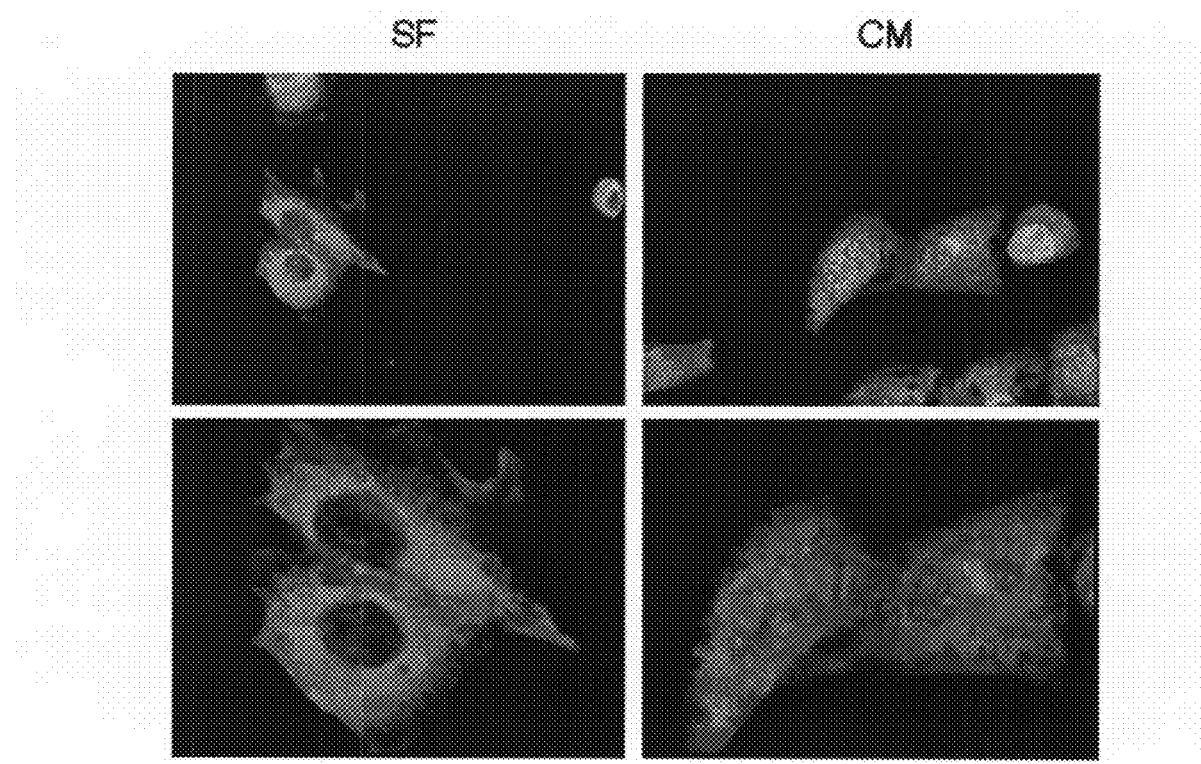
FIG. 3e shows the results of observation of the cellular localization of AIM3 at different proliferation conditions of cells.
SF: cell culture in serum-free media
CM: cell culture in complete media

As shown in FIG. 3e, when the cell growth was suppressed by serum starvation, AIM3 was mainly located in cytoplasm, whereas, when the cell growth was resumed, AIM3 was located in nuclei. Given thus, it could be found that, during the DNA synthetic phase of the cell cycle, AIM3 was not only induced but also translocated into nuclei. These results suggest that AIM3 could have novel functions in the nuclei.

EXAMPLE 5

Determination of Relation Between DNA Damage and AIM3

The damage of DNA by stresses and so on generally induces apoptosis and cell cycle arrest (Zhou B B et al., *Cancer Biol. Ther.*, S(4 Suppl 1):S16-22, 2003). Thus, the present inventors investigated the role of AIM3 in the response of cells to the stress -induced apoptosis and cell growth arrest.

<5-1> Examination of Effect of AIM3 Gene Deletion on Apoptosis Regulation

Using adriamycin that induces DNA damage, the response of AIM3$^{+/-}$ mouse -derived splenocytes to pro-apoptotic stress was examined.

First, the splenocytes were isolated from wild-type mice and AIM3$^{+/-}$ mice. To induce apoptosis, the isolated splenocytes were treated with 0.2 μg/ml of adriamycin (Adr, Sigma) for 2 hours. Then, the cells were cultured with FITC-conjugated annexin V (Roche) for 5 minutes. And then, the cells were washed with PBS and subjected to FACS analysis under a FL-1H detector. In this analysis, 20,000 cells per sample were used.

Figure 4A:
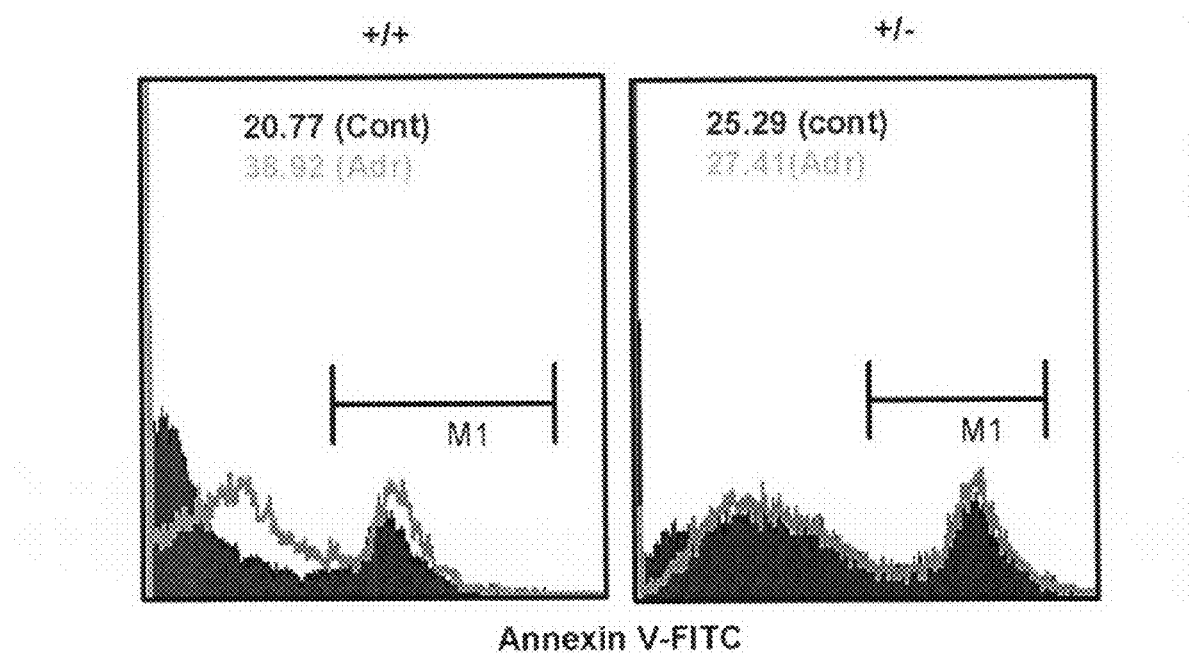
FIG. 4a shows the results of flow cytometry to examine the apoptotic responses of splenocytes of AIM3 heterozygous mice (+/−) to adriamycin treatment (Adr), as compared to those of wild-type mice (+/+).
M1: annexin V-FITC positive populations

As shown in FIG. 4a, apoptotic cells were significantly increased by treatment with adriamycin in the wild-type cells, however the AIM3$^{+/-}$ cells showed the resistance to apoptosis induced by adriamycin. This indicates that AIM3 is required for sensitivity of cell to apoptosis induced by DNA damage. From this, it can be found that AIM3 promotes apoptosis caused by DNA damage.

<5-2> Examination of Change in Cell Growth Caused by Apoptosis-inducer

Figure 4B:
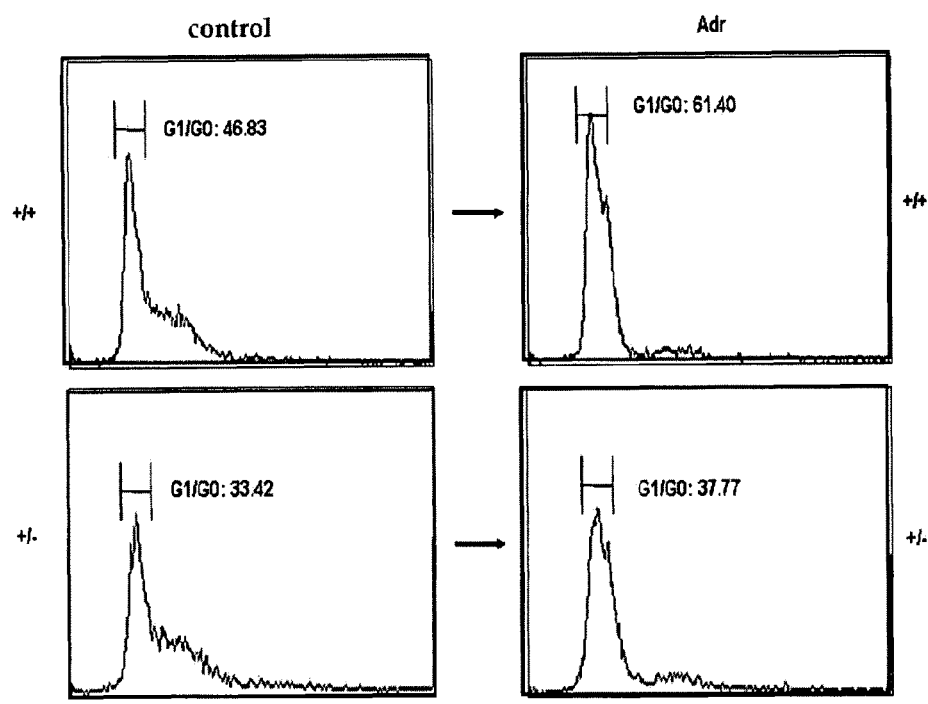
FIG. 4b shows the results of flow cytometry to examine the response of wild-type mice- and AIM3 heterozygous mice (+/−)-derived cells to adriamycin treatment, which caused cell growth arrest.

In order to examine the importance of AIM3 in cell growth arrest caused by adriamycin, flow cytometry was performed. First, the thymocytes were isolated from wild-type mice and AIM3$^{+/-}$ mice, and then treated with 0.2 μg/ml of adriamycin (Adr, Sigma) for 6 hours. Next, the cells were subjected to FACS analysis in the same method as in Example <5-1>. As shown in FIG. 4b, the growth of AIM3$^{+/-}$ mouse cells was slightly suppressed by treatment with adriamycin, whereas that of wild-type mouse cells was arrested.

<5-3> Examination of Change in AIM3 Level Caused by Apoptosis -inducer

It was examined by RT-PCR analysis and Western blot analysis whether the level of AIM3 is affected by treatment with adriamycin.

For this purpose, HCT116 cells were treated with 0.2 μg/ml of adriamycin. Then, the cells were collected at different time and dissolved in Sol D solution (4 M guanidine thiocyanate, 1% laurosarcosine, 25 mM sodium citrate, and 0.1% b -mercaptoethanol). The cell extracts were incubated in acidic phenol and chloroform containing 4% isoamylalcohol, and vortexed. The mixture was centrifuged at 14,000 rpm. The upper layer was collected and added with isopropanol so as to precipitate RNA. The precipitated RNA was washed with 100% ethanol, and 1 μg of RNA was dissolved in distilled water and used as a template for RT-PCR. Then, RT-PCR was performed with primers shown in SEQ ID NO: 8 and SEQ ID NO: 9. The expression level of GADPH was also measured in order to quantitatively compare that of AIM3.

Meanwhile, for Western blot analysis, cells treated with adriamycin were dissolved in RIPA containing protease cocktail. The solution was centrifuged at 14,000 rpm for 30 minutes. 20 μg of the extracted proteins were separated by SDS-PAGE. Then, according to the method described in Park S. G., et al. (Park S. G., et al., *J. Biol. Chem.*, 274:16673-16676, 1999), Western blot analysis was performed using a polyclonal rabbit anti-AIM3 antibody. The expression level of tubulin was also measured in order to quantitatively compare that of AIM3.

As shown in FIG. 4c, both the transcription and translation of AIM3 were induced in response to adriamycin. Moreover, the induction of AIM3 was also observed by other DNA-damaging agents, such as UV, actinomycin D (Act.D) and cisplatin (CDPP) (data not shown). Particularly, AIM3 was induced within 5-10 minutes after exposure to UV or adriamycin (data not shown). These results indicate that AIM3 is functionally involved in signal transduction pathways which respond to DNA repair caused by DNA replication or DNA damage.

<5-4> Cellular Localization of AIM3 Upon DNA Damage

Figure 4D:
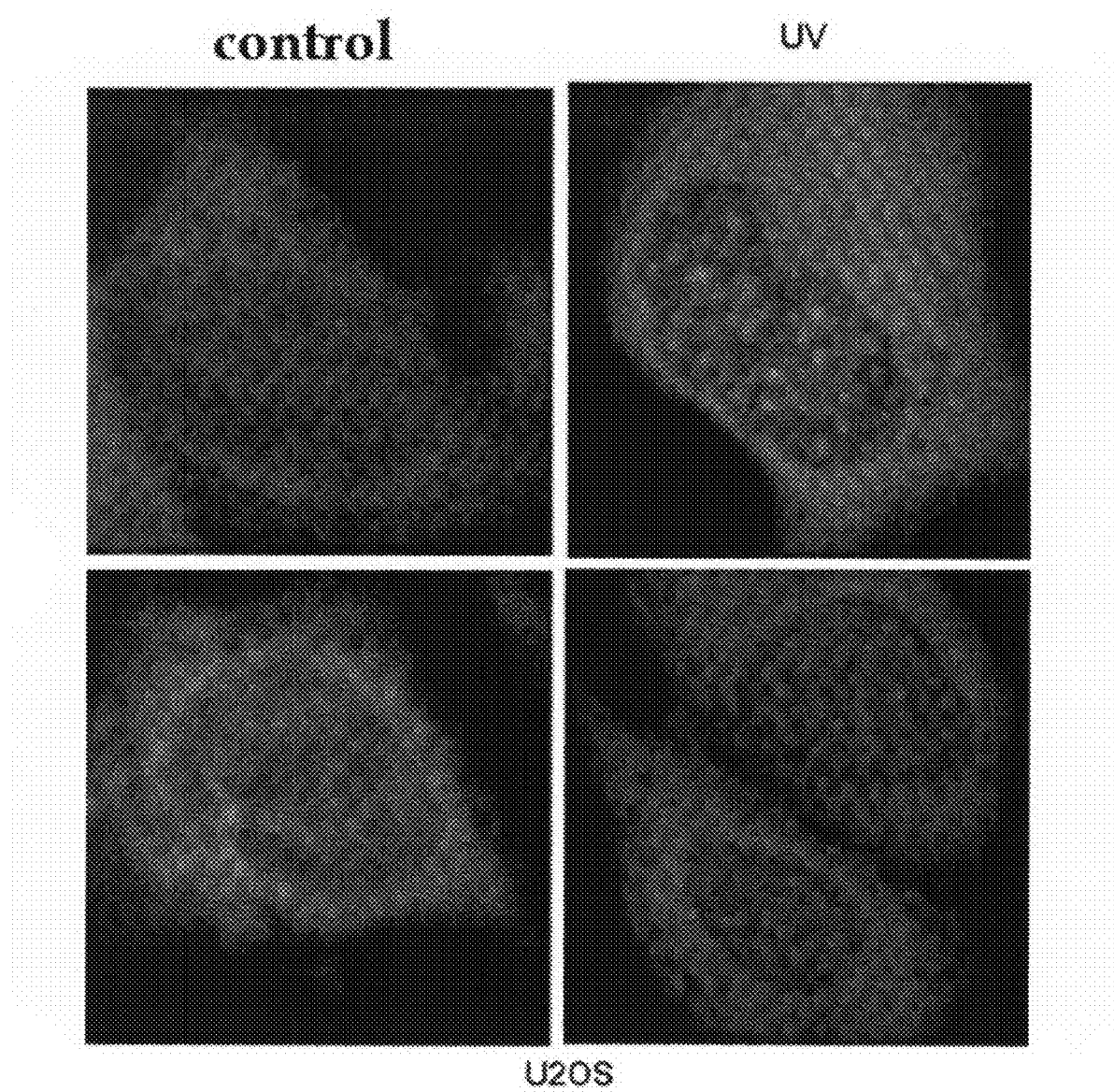
FIG. 4d shows the results of immunofluorescent staining to observe the cellular localization of AIM upon exposure to UV.

The cellular localization of AIM3 upon DNA damage was examined using U2OS cells containing large nuclei. The U2OS cells (osteosarcoma cell line) were treated with 254-nM wavelength UV-C (UV cross linker) at 50 J/m$^2$. The cells were cultured in a complete medium for 30 minutes and collected. Then, the same method as in Example <4-3> was performed so as to examine the cellular localization of AIM3 by immunofluorescent staining. As a result, as shown in FIG. 4d, the UV-irradiated cells showed a remarkable increase in nuclear foci formed by AIM3.

All of these results indicate that AIM3 is involved in responses to DNA damage induced by genotoxic stress.

EXAMPLE 6

Identification of Relation Between Cell Proliferation and AIM3

The present inventors found in <Example 4> that loss of AIM3 made cell cycle faster and AIM3 was highly induced in the DNA synthetic phase. Thus, it was examined whether AIM3 is also involved in cell proliferation.

<6-1> Examination of Change in Cell Proliferation Caused by Deletion of AIM3 Gene a) Thymidine Incorporation Mouse embryonic fibroblasts (MEFs, E14.5d) isolated from wild-type mice and AIM3$^{+/-}$ mice were cultured in a medium containing 1 μCi/ml [$^3$H] thymine. The cultured cells were washed with cold PBS and incubated in 10% TCA solution for 30 minutes so as to precipitate nucleic acids. Then, the cells were dissolved in 0.1 N NaOH, and the amount of radioactive thymidine incorporated in the precipitate was quantified by a liquid scintillation counter. The experiments were repeated three times and the data were averaged.

Figure 5A:
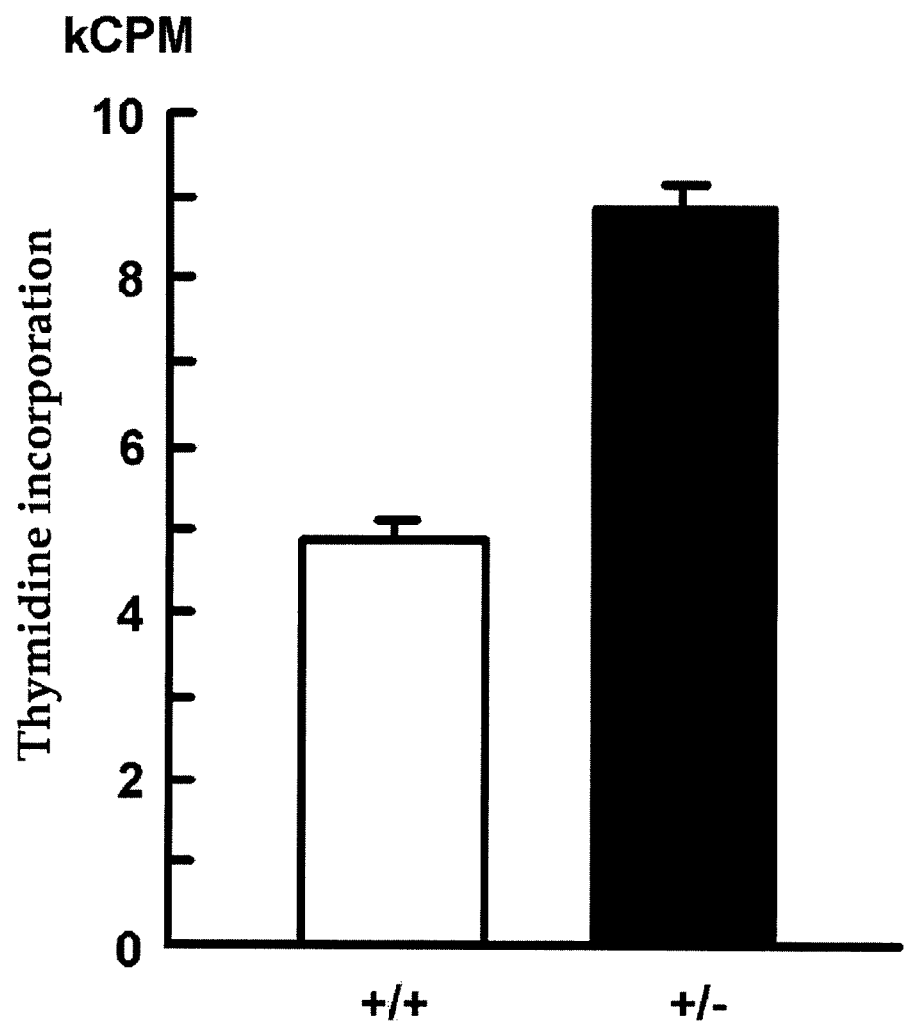
FIG. 5a illustrates the results of thymidine incorporation to measure the cell proliferation rate of mouse embryonic fibroblasts (MEFs) isolated from wild-type mice (+/+) and AIM3 heterozygous mice (+/−).

As a result, as shown in FIG. 5a, MEFs isolated from the AIM3$^{+/-}$ mice had a higher proliferation rate than the wild-type MEFs.

b) In Situ Immunofluorescence Staining

From AIM3$^{+/-}$ mice, the intestines, testes, spleens and thymuses were isolated. Then, to examine the cell proliferation rate of the isolated tissues, in situ immunofluorescence staining was performed using Ki-67, cell proliferation marker (Gerdes J. et al., *J. Immunol.*, 133:1710-1715, 1984).

Figure 5B:
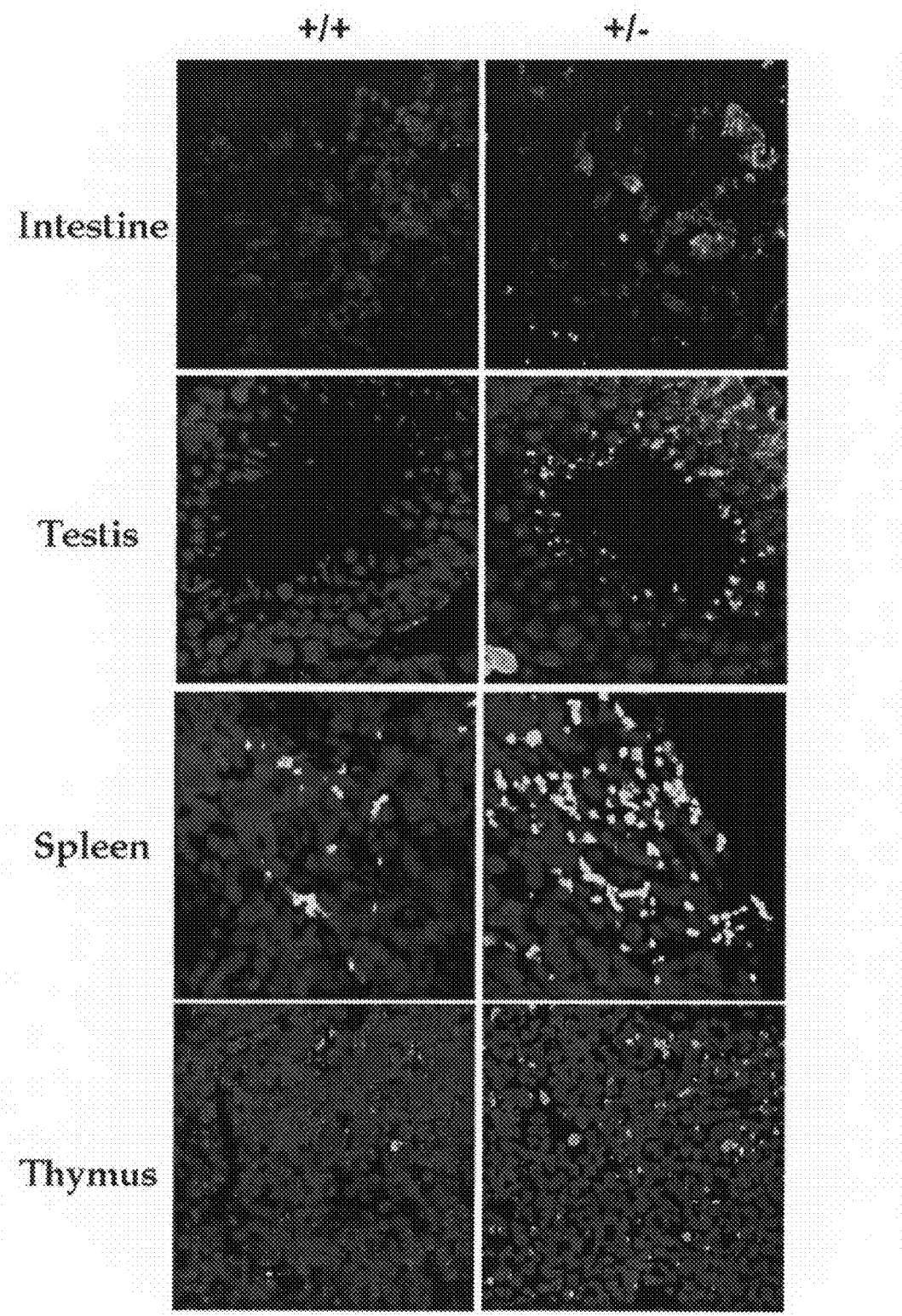
FIG. 5b illustrates the results of immunofluorescent staining using an anti-Ki67 antibody (green color), to measure the cell proliferation rate of various tissues isolated from wild-type mice (+/+) and AIM3 heterozygous mice (+/−).

As a result, as shown in FIG. 5b, the proliferation of cells in the AIM3$^{+/-}$ mouse-derived tissues was higher than that in the wild-type mouse-derived tissues.

<6-2> Examination of Change in Cell Proliferation Rate with Increase in AIM3 Expression The present inventors found in Example <6-1> that a reduction in the expression of AIM3 resulted in an increase in cell proliferation. Thus, it was examined whether an increase in the expression of AIM3 results in the suppression of cell proliferation.

The AIM3 gene (SEQ ID NO: 2) was inserted into a pcDNA3 (Invitrogen) vector so as to prepare an AIM3 expression vector. Then, the expression vector was transfected into HCT116 cells (human colon adenocarcinoma cell line). The cell proliferation rate of the transfected cells was examined in the same method as in the part a) of Example <6-1>. As a control group, HCT116 cells transfected with pcDNA3 vector containing no AIM3 gene (empty vector; EV) were also used.

Figure 5C:
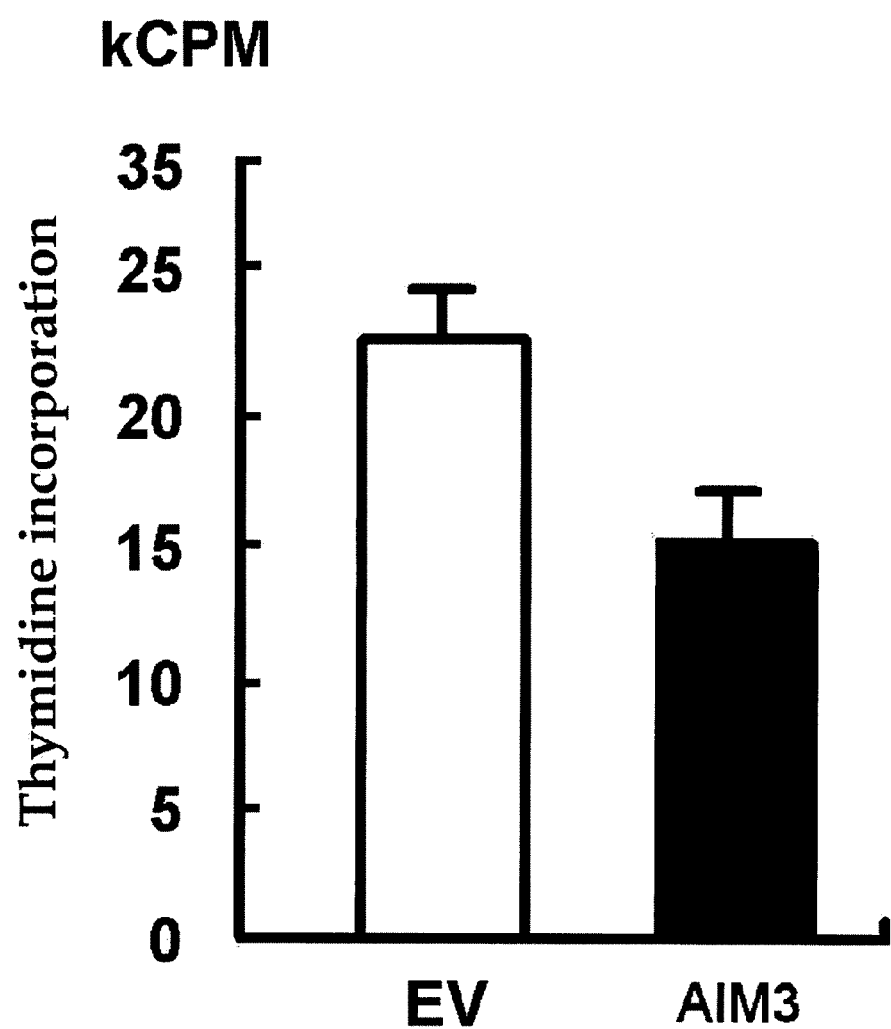
FIG. 5c illustrates the results of thymidine incorporation to measure the proliferation rate of cells transfected with an AIM3 gene.

As a result, as shown in FIG. 5c, proliferation of cells was reduced in the cells introduced with the AIM3 gene. This suggests that AIM3 shows anti-proliferation activity against tumor cells.

EXAMPLE 7

Identification of Function of AIM3 as Upregulator of p53

Tumor suppressor protein p53 plays a major role in regulation of DNA damage-induced cell cycle arrest and apoptosis (Levine, *Cell*, 88:323-331, 1997; Vousden, *Cell*, 103:691-694, 2000). Thus, the functional relation between AIM3 and p53 was examined.

<7-1> Measurement of p53 Level Caused by AIM3

The expression levels of p53 and AIM3 in mouse embryonic fibroblasts (MEFs) isolated from AIM3$^{+/-}$ mice and wild-type mice were measured with Western blot analysis according to the same method as in Example <5-3>. Also, the expression levels of AIM3 and p53 in the transfected HCT116 were measured with Western blot analysis after the AIM3 expression vector prepared in Example <6-2> was transfected into HCT116 cells.

As a result, as shown in FIG. 6a, the expression level of p53 in the MEFs of the AIM3$^{+/-}$ mice was lower than that in the MEFs of the wild-type mice. Meanwhile, the level of p53 in the HCT116 cells transfected with the AIM3 gene was increased as compared to that in a control group cells transfected with an empty vector containing no AIM3 gene. This indicates that the ectopic expression of AIM3 elevates the expression of p53.

<7-2> Measurement of p21 Level Caused by AIM3

In order to determine whether the increase of AIM3 would enhance the p53-dependent transcription, the AIM3-dependent transcription of p21 known as a target gene of p53 was examined.

The HCT116 cells transfected with the AIM3 gene (1 μg/ml) in Example <7-1> were cultured for 24 hours. Then, RT-PCR analysis was performed in the same method as in Example <5-3>. As a result, as shown in FIG. 6b, the expression of p21 in the HCT116 cells transfected with the AIM3 gene was enhanced.

<7-3> Measurement of p21 Level Caused by AIM3 and Adriamycin

Thereafter, in order to examine the effect of AIM3 and/or adriamycin on the transcription of p21, luciferase assay was performed using a vector containing a p21 promoter fused to luciferase gene.

HCT116 cells were co-transfected with a pGL-3 vector (Promega) engineered that the luciferase gene would be expressed under p21 promoter, and a recombinant AIM3 expression vector (1.2 μg/ml) containing the AIM3 gene. Also, control group cells were co-transfected with the pGL-3 vector and an empty vector containing no AIM3 gene. Then, the transfected cells of each group were treated with 0.2 μg/ml of adriamycin for 2 hours. After cells were lyzed, the cell extract were incubated with substrate of luciferase for 30 minutes at room temperature. 5 μl of each sample was transferred to luminometer plate and luciferase activity was measured following the manufacturer's protocol (Promega).

As a result, as shown in FIG. 6c, the luciferase activity regulated by the p21 promoter was highly increased by transfection with AIM3 and the luciferase activity was further increased by the additional treatment with adriamycin.

<7-4> Identification of Relation Between Anti-Proliferation Activity of AIM3 and p53 and p21

Examples <7-1> and <7-2> demonstrated that the expressions of p53 and p21 depend on AIM3. Thus, it was examined whether AIM3 suppresses the proliferation of tumor cells via p53 and p21.

The AIM3 expression vector or empty vector (2 μg/Ml) prepared in Example <6-2> was transfected into each of HCT116 cells (human colon adenocarcinoma cell line), p53-null HCT116 cells and p21-null HCT116 cells. Then, the proliferation rate of each of the transfected cells was examined according to the same method as in the part a) of Example <6-1>.

As a result, as shown in FIG. 6d, the anti-proliferation activity of AIM3 was abolished by the absence of functional p53 and p21. This indicates that AIM3 suppresses the proliferation of tumor cells via p53 and p21.

<7-5> Measurement of Reduction in p53 Level Caused by Inhibition of AIM3 Expression The present inventors inhibited the expression of AIM3 by the use of antisense-AIM3 (As-AIM3) and then examined if the induction of p53 is influenced by the inhibition of the AIM3 expression.

First, using primers shown in SEQ ID NO: 10 and SEQ ID NO: 11, the N-terminal 176-bp region of the ATG-containing AIM3 gene was amplified by PCR. The PCR product was inserted into a pcDNA 3.1 vector in reverse orientation. 2 μg/ml of a vector containing antisense-AIM3 was transfected into HCT116 cells. The transfected cells were cultured for 24 hours. Then, the cells were treated with UV and 0.2 μg/ml of adriamycin, respectively. Next, using an anti-AIM3 antibody or an anti-p53 antibody (Santacruz), Western blot analysis was performed in the same method as in Example <2-5>. At this time, the expression level of actin was also measured in order to quantitatively compare the expression level of AIM3 and p53.

As a result, as shown in FIG. 6e, the level of p53 was increased by treatment with UV or adriamycin, whereas the suppression of AIM3 by As-AIM3 inhibited the induction of p53. This indicates that AIM3 is required for increasing the expression of p53. Moreover, the transcription of PUMA, an immediate early target gene of p53, was also increased by irradiation with UV, and its induction was blocked when AIM3 was suppressed by As-AIM3 (data not shown).

These results indicate that AIM3 is an important upregulator of p53 that mediates the induction of p53 caused by DNA damage.

EXAMPLE 8

Determination of Mechanism of AIM3

ATM/ATR are substances directly activating p53 in response to DNA damage (Canman et al., *Science*, 281:1677-1679, 1998; Banin S et al., *Science*, 11; 281 (5383):1674-7, 1998). Thus, the present inventors examined whether AIM3 acts via ATM/ATR.

<8-1> Analysis of Caffeine-Induced Inhibition of Anti-Proliferation Activity of AIM3

In order to explore the possibility, that AIM3 can regulate p53 via ATM/ATR, the present inventors first checked the anti-proliferation activity of AIM3 in the presence of caffeine known as an inhibitor of ATM/ATR. HCT116 cells were transfected with each of the AIM3 expression vector and the empty vector (2 μg/ml, respectively) for 24 hours. Then, the cells were added with 20 mM caffeine and cultured for 4 hours. Control group cells were added with PBS. The cell proliferation rate of the cells of each group was examined according to the same method as in the part a) of Example <6-1>. As a result, as shown in FIG. 7a, the anti-proliferation activity of AIM3 was abolished by caffeine, an inhibitor of ATM/ATR. This demonstrates that AIM3 has anti-proliferation activity via ATM/ATR.

<8-2> Analysis of Caffeine-Induced Inhibition of Apoptosis Induced by AIM3

Thereafter, the present inventors checked whether AIM3-induced apoptosis is inhibited by caffeine, an inhibitor of ATM/ATR. HCT116 cells were transfected with each of the AIM3 expression vector or the empty vector (4 μg/ml, respectively) for 24 hours. Then, the cells were added with 20 mM caffeine and cultured for 12 hours. Control group cells were added with PBS. After staining the cells with PI, we checked apoptosis with measuring for the portion (%) of sub-G1 cells. As a result, as shown in FIG. 7b, apoptosis was induced by the expression of AIM3, and this effect was relieved by treatment with caffeine.

<8-3> Analysis of Caffeine-induced Inhibition of AIM3-dependent p53 Induction

Thereafter, the present inventors examined whether the AIM3-induced expression of p53 is inhibited by caffeine. First, HCT116 cells were transfected with each of the AIM3 expression vector and the empty vector (2 μg/ml, respectively) for 24 hours. Then, the cells were added with 20 mM caffeine and cultured for 12 hours. Control group cells were added with PBS and cultured. Then, in order to examine the levels of AIM3 and p53, Western blot analysis was performed in the same method as in Example <7-5>. At this time, the expression level of actin was also measured in order to quantitatively compare the expression levels of AIM3 and p53.

As a result, as shown in FIG. 7c, the AIM3-induced expression of p53 was suppressed by caffeine. Moreover, the expression of PUMA, a target gene of p53, was also induced by AIM3, however it was suppressed by caffeine (data not shown). These results indicate that ATM/ATR play an important role in the AIM3-dependent induction of p53.

<8-4> Analysis of KD-ATM-induced Inhibition of AIM3-dependent p53 Induction

In order to more specifically determine that ATM/ATR play an important role in the AIM3-dependent induction of p53, HCT116 cells were transfected with the kinase-dead domain of ATM (KD-ATM) (Canman et al., Science, 281: 1677-1679, 1998). The KD-ATM suppresses specifically the activity of ATM.

First, each of vectors containing the KD-ATM domain or wild-type ATM respectively (provided by Micheal Kastan, St. Jude Children's Hospital), was introduced into HCT116 cells with the AIM3 expression vector (2 μg/ml). Also, as a control group for the AIM3 expression, each of these vectors was introduced into HCT116 with the empty vector containing no AIM3 gene. Then, the expression levels of p53 and AIM3 in the cells of each group were examined by Western blot analysis according to the same method as in Example <6-5>. At this time, the expression level of actin was also measured in order to quantitatively compare the expression levels of AIM3 and p53.

As a result, as shown in FIG. 7d, the p53 induction caused by an increase in the AIM3 expression was blocked by KD-ATM, whereas not by the wild-type ATM. These results further support that ATM is required for the AIM3-dependent induction of p53.

All of these results confirm that AIM3 has anti-proliferation activity, apoptosis-inducing activity and p53-upregulating activity, via ATM/ATR.

EXAMPLE 9

Analysis of ATM/ATR Activation Caused by AIM3

<9-1> Analysis of Interaction Between AIM3 and ATM a) Co-immunoprecipitation

In order to examine the interaction between AIM3 and ATM, co-immunoprecipitation was performed. First, from HCT116 cells treated with each of UV and 0.2 μg/ml adriamycin, proteins were extracted at different times. The protein extracts were incubated with normal IgG and protein A/G-agarose for 2 hours and centrifuged to remove nonspecific IgG binding proteins. After centrifugation, the supernatant was taken, added with 2 μg of an anti-ATM antibody (Santacruz) and incubated at 4° C. for 2 hours with agitation. And then, protein A/G-agarose was added. After washing twice with cold PBS and once with PIRA, the precipitates were dissolved in an SDS-sample buffer, and separated by 6% SDS-PAGE. The proteins separated by the SDS-PAGE were transferred to a PVDF membrane, followed by reacted orderly with an anti-AIM3 single antibody and a horseradish peroxidase conjugated secondary antibody.

As a result, as shown in FIG. 8a, the interaction between AIM3 and ATM was increased within 5 minutes in response to UV and adriamycin. The dissociation kinetics of AIM3 appeared to be much slower in adriamycin-treated cells possibly because adriamycin is present in the media throughout the cultivation while UV stress would affect the cells only temporarily.

b) In Vitro Pull Down Assay

To examine the direct interaction between AIM3 and ATM, GST full-down assay was performed.

First, AIM3 was expressed as GST fusion protein and purified according to the manufacturer's protocol (Pharmacia). Meanwhile, since it was difficult to synthesize the whole ATM due to its large size, the present inventors tested the interaction between the functional domain of ATM and AIM3. For this purpose, a fragment consisting of 612 amino acids, including the FAT domain of an ATM structure, was amplified by PCR with primers shown in SEQ ID NO: 12 and SEQ ID NO: 13. Also, a fragment (control group) consisting of 145 amino acids, including the C-terminal domain, was amplified by PCR with primers shown in SEQ ID NO: 14 and SEQ ID NO: 15. Then, the amplified PCR products were subcloned into pcDNA3.1 (Invitrogen), a vector suitable for in vitro transcription and transition. At this time, the protein was synthesized by in vitro translation in the presence of radioactive methionine. 10 μl of the synthesized TNT product was incubated with the GST- or GST-AIM3 fusion protein-immobilized glutathion-sepharose beads for 5 minutes. Then, the beads were washed six times with a binding buffer (PBS containing 0.2% sarcosine and 0.2% Triton X100), and dissolved in 10% SDS-PAGE. The binding of the GST-fused AIM3 to each domain was determined by autoradiography.

As a result, as shown in FIG. 8b, the GST-fused AIM3 protein bound to the FAT domain, a functional domain, but not to the C-terminal domain of ATM. This suggests that AIM3 interacts directly with ATR.

<9-2> Analysis of Interaction Between AIM3 and ATR

The FAT domain is found in not only ATM but also ATR (Abraham R, *Genes Dev.*, 15:2177, 2001). Thus, the interaction between AIM3 and ATR was tested by co-immunoprecipitation.

First, the 293 cell was transfected with an ATR vector (provided by Elledge S., Harvard University) containing flag-tagged ATR. The transfected 293 cell was treated with UV, from which proteins were extracted at different time. Next, the same method as the part a) of Example <9-1> was performed except that an anti-FLAG antibody (Sigma) was used in place of the anti-ATM antibody.

As a result, as shown in FIG. 8c, AIM3 was co-immunoprecipitated with the flag-tagged ATR, and this interaction was further enhanced upon exposure to UV. This suggests that AIM3 also interacts with ATR as it acts on ATM.

Accordingly, it could be found from the above results that AIM3 interacts directly with ATR/ATM.

<9-3> Analysis of ATM/ATR Activation by AIM3

The present inventors examined whether the activity of ATM/ATR is enhanced by the association with AIM3.

a) Measurement of Phosphorylation Level of H2AX in AIM3$^{+/-}$ Mouse-derived Cells The activity of ATM/ATR was examined using H2AX known as a substrate of ATM/ATR (Burma et al., *J. Biol. Chem.*, 276: 42462-42467, 2001; Ward, I. M. et al., *J. Biol. Chem.*, 276: 47759-47762, 2001; Irene M. Ward et al., *J. Biol. Chem.*, 279(11):9677-9680, 2004).

After isolating splenocytes and thymocytes from wild-type mice and AIM3+/−mice, the phosphorylation level of H2AX in the isolated cells was measured by Western blot analysis in the same method as in Example <7-5>. As a result, as shown in FIG. 9a, the phosphorylation of H2AX (p-H2AX) was significantly reduced in the AIM3$^{+/-}$ mice-derived cells.

b) Analysis of H2AX Phosphorylation Inhibition Caused by Antisense Aim3

Thereafter, the present inventors treated cells with VP16, a DNA-damaging agent (Clarke et al., *Nature*, 362:849-852, 1993), and examined whether the phosphorylation of H2AX is inhibited by AIM3 inhibition in the presence of antisense-ATM3 (As-AIM3). Antisense AIM3-containing vector (2 μg/ml) prepared in Example <7-5> was introduced into HCT116 cells. The transfected cells were cultured for 24 hours and then treated with 100 μM of VP16 (Sigma), an apoptosis-inducing agent, for 4 hours. Next, using each of an anti-53 antibody, an anti-AIM3 antibody and an anti-p-H2AX antibody (Cell signaling), Western blot analysis was performed in the same method as in Example <7-5>. At this time, the expression level of actin was also measured in order to quantitatively compare that of each protein. As a result, as shown in FIG. 9b, the phosphorylation of H2AX was enhanced by treatment with VP16, but inhibited by the expression of antisense-AIM3.

c) Analysis of Effect of AIM3 on ATM Activation

In order to analyze the effect of AIM3 on the autophosphorylation of ATM, the present inventors examined the phosphorylation of ATM and its target proteins, p53 and chk2, by Western blot analysis. Cells isolated from wild-type mice and AIM3$^{+/-}$ mice were treated with 0.2 μg/ml of adriamycin. Then, using each of an anti-phospho-serine antibody of ATM, an anti-p53 antibody and an anti-chk2 antibody, Western blot analysis was performed (Bakkenist and Kastan, *Nature*, 421: 499-506, 2003). As a result, as shown in 9c, the phosphorylation of ATM and its target proteins in the wild-type cells was enhanced by treatment with adriamycin, whereas that in the AIM3$^{+/-}$ cells was inhibited.

All of these results indicate that AIM3 is required for the activation of ATM/ATR and its target proteins.

EXAMPLE 10

Identification of Functional Relation Between Cancers and AIM3

<10-1> Measurement of Expression Level of AIM3 in Human Cancer Cell Lines a) RT-PCR Analysis To identify the functional relation between human cancers and AIM3, the present inventors measured the level of AIM3 in various cancer cell lines shown in Table 4, by RT-PCR. The RT-PCR analysis was performed in the same method as in Example <5-3>.

TABLE 4

| | Cell line name | Derived from | p53 function |
|---|---|---|---|
| 1 | HCT116 (human colon carcinoma cell line) | Colon | + |
| 2 | SW480 (human colon cancer cell lines) | | − |
| 3 | H23 (non-small cell lung cancer cell line) | Lungs | − |
| 4 | H157 (non-small cell lung cancer cell line) | | − |
| 5 | A549 (human lung carcinoma cell line) | | + |
| 6 | H460 (human lung carcinoma cell line) | | + |
| 7 | Raji (B-cell leukemia cell line) | Lymphocytes | +/− |
| 8 | K-562 (human leukemia cell line) | | − |

As a result, as shown in FIG. 10a, the level of expression of AIM3 was lower in HCT116, A549 and H460 cell lines. Specifically, the level of AIM3 was low in the cells containing active p53 (p53(+), i.e., HCT116, A549 and H460 cell lines), while it was normal in the cells lacking active p53 (p53(−), i.e., SW460, H23, H157 and K-562 cell lines). Also in Raji cells containing partially activated p53 (Bhatia et al., *FASEB J.*, 7:951-956, 1993), the level of AIM3 was in the middle of that of p53(+) cells and p53(−) cells. These results suggest that the expression level of AIM3 has a functional relation with p53. Also, these results further support that the aberration in either one of AIM3 or p53 may be sufficient to transform the cells, and AIM3 and p53 work in the same signal transduction pathway.

Furthermore, the expression level of AIM3 was analyzed by Western blot only in the lung cancer cell lines among the cell lines in Table 4. And the results coincided with that of the above RT-PCR analysis (data not shown).

These results suggest that the expression level of AIM3 in some cancer cell lines is reduced.

b) Genomic PCR Analysis

To have a clue to the possible cause for the low expression level of AIM3 in some cancer cell lines, the present inventors compared the DNA content for the AIM3 gene by PCR. On H157, H460, HCT116, A549 and DU145 cell lines, genomic DNA analysis was performed in the same method as in Example <2-2>. As a control group, an actin gene was used.

As a result, as shown in FIG. 10b, the H460 and A549 cell lines contained less amount of AIM3 DNA than that of other cell lines. This indicates that the two cell lines may have lost one allele for AIM3.

<10-2> Measurement of Expression Levels of AIM3 and p21 in Tissues Isolated from Cancer Patients Thereafter, the expression levels of AIM3 and p21 in the tissues isolated from cancer patients were examined. Total RNA was extracted from the leukocytes of 9 leukemia patients (five patients: acute promyelocytic leukemia (APML), and four patients: chronic myelocytic leukemia (CML)). Then, RT-PCR was performed in the same method as in Example <5-3>. In RT-PCR for p21, primers shown in SEQ ID NO: 16 and SEQ ID NO: 17 were used.

As a result, as shown in FIG. 10c, the low level of AIM3 was observed in the tissues of 3 patents. In this case, the expression of p21, a target gene of p53, was also strongly suppressed. This demonstrates again that AIM3 is functionally involved in the regulation of p53.

<10-3> Comparative Measurement of Expression Levels of AIM3 in Normal Tissue and Cancer Region from Liver Cancer Patients Since solid tumors were also found in AIM3$^{+/-}$ mice although the frequency was much lower, the present inventors also compared the expression levels of AIM3 in the cancer region with that in normal tissue isolated from liver cancer patients by RT-PCR. As a control group, the expression level of actin was also measured. From the analysis of 25 different patient samples, a cancer-specific reduction of AIM3 was observed in 12 samples. The results for exemplary 8 samples are shown in FIG. 10d.

All these results in this Example suggest that a low level of expression of AIM3 is associated with various human cancer cell lines and patient tissues at high frequency. Also, these results indicate that the measurement of the expression level of AIM3 allows for the diagnosis of cancers.

INDUSTRIAL APPLICABILITY

As described above, it was found in the present invention that AIM3 acts as a powerful tumor suppressor. The AIM3 protein binds to the FAT domain of ATM/ATR so as to activate ATM/ATR, thus inducing the expression of p53, tumor suppressor protein. Accordingly, the AIM3 protein or a nucleic acid encoding the protein will be useful for cancer therapy. Furthermore, it will be useful as targets for the development of anticancer drugs and as diagnostic markers of various cancers.

What is claimed is:

1. A method for inhibiting the proliferation of tumor cells, comprising administering to a cell, tissue or individual an effective amount of an isolated nucleic acid encoding an AIM3 polypeptide having the amino acid sequence shown in SEQ ID NO: 1, wherein said cell, tissue or individual comprises tumor cells selected from the group consisting of colon cancer cells, lung cancer cells, leukemia cells, liver cancer cells, breast cancer cells, cervical cancer cells, and prostate cancer cells, wherein the isolated nucleic acid is expressed in the cell, tissue or individual, and wherein the tumor cells have functional p53 or p21.

2. The method of claim 1, wherein said inhibiting of the proliferation of tumor cells is mediated by upregulation of the activity of p53 by said AIM3 polypeptide.

3. A method for inhibiting the proliferation of tumor cells, comprising administering to a subject requiring treatment an effective amount of an isolated nucleic acid encoding an AIM3 polypeptide having the amino acid sequence shown in SEQ ID NO: 1, wherein said subject comprises tumor cells selected from the group consisting of colon cancer cells, lung cancer cells, leukemia cells, liver cancer cells, breast cancer cells, cervical cancer cells, and prostate cancer cells, wherein the isolated nucleic acid is expressed in the subject, and wherein the tumor cells have functional p53 or p21.

4. The method of claim 3, wherein said subject is a human.

* * * * *

SEQUENCE LISTING

```
<160> NUMBER OF SEQ ID NOS: 17

<210> SEQ ID NO 1
<211> LENGTH: 174
<212> TYPE: PRT
<213> ORGANISM: Homo sapiens

<400> SEQUENCE: 1

Met Ala Ala Ala Ala Glu Leu Ser Leu Leu Glu Lys Ser Leu Gly Leu
 1               5                   10                  15

Ser Lys Gly Asn Lys Tyr Ser Ala Gln Gly Glu Arg Gln Ile Pro Val
            20                  25                  30

Leu Gln Thr Asn Asn Gly Pro Ser Leu Thr Gly Leu Thr Thr Ile Ala
        35                  40                  45

Ala His Leu Val Lys Gln Ala Asn Lys Glu Tyr Leu Leu Gly Ser Thr
    50                  55                  60

Ala Glu Glu Lys Ala Ile Val Gln Gln Trp Leu Glu Tyr Arg Val Thr
65                  70                  75                  80

Gln Val Asp Gly His Ser Ser Lys Asn Asp Ile His Thr Leu Leu Lys
                85                  90                  95

Asp Leu Asn Ser Tyr Leu Glu Asp Lys Val Tyr Leu Thr Gly Tyr Asn
            100                 105                 110

Phe Thr Leu Ala Asp Ile Leu Leu Tyr Tyr Gly Leu His Arg Phe Ile
        115                 120                 125

Val Asp Leu Thr Val Gln Glu Lys Glu Lys Tyr Leu Asn Val Ser Arg
    130                 135                 140

Trp Phe Cys His Ile Gln His Tyr Pro Gly Ile Arg Gln His Leu Ser
145                 150                 155                 160

Ser Val Val Phe Ile Lys Asn Arg Leu Tyr Thr Asn Ser His
                165                 170

<210> SEQ ID NO 2
<211> LENGTH: 525
<212> TYPE: DNA
<213> ORGANISM: Homo sapiens

<400> SEQUENCE: 2
```

-continued

```
atggcggcgg ccgcagagtt gtcgctactg gagaagtccc tgggactgag taagggggaat      60 aaatacagtg ctcagggcga gcgacagatt ccagttcttc agacaaacaa tggtccaagt     120
ctaacaggat tgactactat agcagctcat ctagtcaagc aagccaacaa agaatatttg     180
ctggggagta ctgcagaaga aaaagcaatc gttcagcagt ggttagaata cagggtcact     240
caagtagatg ggcactccag taaaaatgac atccacacac tgttgaagga tcttaattca     300
tatcttgaag ataaagtcta ccttacaggg tataacttta cattagcaga tatactattg     360
tactatggac ttcatcgctt tatagttgac ctgacagttc aagaaaagga gaaatatctt     420
aatgtgtctc gctggttttg tcacattcag cattatccag gcatcaggca acatctgtct     480
agtgttgtct tcatcaagaa cagactatat actaattccc actga                     525
```

<210> SEQ ID NO 3
<211> LENGTH: 29
<212> TYPE: DNA
<213> ORGANISM: Artificial Sequence
<220> FEATURE:
<223> OTHER INFORMATION: p18F-1 primer for AIM3

<400> SEQUENCE: 3
gccggacttc ctgctcaatc aaggtccta                                        29

<210> SEQ ID NO 4
<211> LENGTH: 32
<212> TYPE: DNA
<213> ORGANISM: Artificial Sequence
<220> FEATURE:
<223> OTHER INFORMATION: p18R-1 primer for AIM3

<400> SEQUENCE: 4
ctagcgggtg gataagtagt agtttcctca tg                                    32

<210> SEQ ID NO 5
<211> LENGTH: 27
<212> TYPE: DNA
<213> ORGANISM: Artificial Sequence
<220> FEATURE:
<223> OTHER INFORMATION: LTR primer for gene trap vector

<400> SEQUENCE: 5
cgttacttaa gctagcttgc cacctac                                          27

<210> SEQ ID NO 6
<211> LENGTH: 32
<212> TYPE: DNA
<213> ORGANISM: Artificial Sequence
<220> FEATURE:
<223> OTHER INFORMATION: p18F-2 primer

<400> SEQUENCE: 6
catgaggaaa ctactactta tccacccgct ag                                    32

<210> SEQ ID NO 7
<211> LENGTH: 32
<212> TYPE: DNA
<213> ORGANISM: Artificial Sequence
<220> FEATURE:
<223> OTHER INFORMATION: p18R-2 primer

<400> SEQUENCE: 7
ccttcagcag agtctgggtg tcttctttac tg                                    32

```
<210> SEQ ID NO 8
<211> LENGTH: 22
<212> TYPE: DNA
<213> ORGANISM: Artificial Sequence
<220> FEATURE:
<223> OTHER INFORMATION: p18-AAAf primer for AIM3 quantitation

<400> SEQUENCE: 8
atgggtccaa gtctaacagg at                                              22

<210> SEQ ID NO 9
<211> LENGTH: 22
<212> TYPE: DNA
<213> ORGANISM: Artificial Sequence
<220> FEATURE:
<223> OTHER INFORMATION: p18-AAAr primer for AIM3 quantitation

<400> SEQUENCE: 9
tgtcaggtct tctataaagc ga                                              22

<210> SEQ ID NO 10
<211> LENGTH: 20
<212> TYPE: DNA
<213> ORGANISM: Artificial Sequence
<220> FEATURE:
<223> OTHER INFORMATION: AIM3 antisense F1 primer for antisense AIM3

<400> SEQUENCE: 10
tctgccagct acggccggaa                                                 20

<210> SEQ ID NO 11
<211> LENGTH: 24
<212> TYPE: DNA
<213> ORGANISM: Artificial Sequence
<220> FEATURE:
<223> OTHER INFORMATION: AIM3 antisense R3 primer for antisense AIM3

<400> SEQUENCE: 11
ggcttgcttg actagatgag ctgc                                            24

<210> SEQ ID NO 12
<211> LENGTH: 21
<212> TYPE: DNA
<213> ORGANISM: Artificial Sequence
<220> FEATURE:
<223> OTHER INFORMATION: FAT-sense primer for FAT

<400> SEQUENCE: 12
atggccaagg tagctcagtc t                                               21

<210> SEQ ID NO 13
<211> LENGTH: 21
<212> TYPE: DNA
<213> ORGANISM: Artificial Sequence
<220> FEATURE:
<223> OTHER INFORMATION: FAT-antisense primer for FAT

<400> SEQUENCE: 13
tctgcttctt ctggctacct c                                               21

<210> SEQ ID NO 14
<211> LENGTH: 21
<212> TYPE: DNA
<213> ORGANISM: Artificial Sequence
<220> FEATURE:
<223> OTHER INFORMATION: C-terminal-ATM sense primer

<400> SEQUENCE: 14
```

```
attacgggtg ttgaaggtgt c                                              21

<210> SEQ ID NO 15
<211> LENGTH: 18
<212> TYPE: DNA
<213> ORGANISM: Artificial Sequence
<220> FEATURE:
<223> OTHER INFORMATION: C-terminal-ATM antisense primer

<400> SEQUENCE: 15
ccaagctttt cctgggaa                                                  18

<210> SEQ ID NO 16
<211> LENGTH: 22
<212> TYPE: DNA
<213> ORGANISM: Artificial Sequence
<220> FEATURE:
<223> OTHER INFORMATION: p21-1 primer for p21

<400> SEQUENCE: 16
atgtcagaac cgggtgggga tg                                             22

<210> SEQ ID NO 17
<211> LENGTH: 22
<212> TYPE: DNA
<213> ORGANISM: Artificial Sequence
<220> FEATURE:
<223> OTHER INFORMATION: p21-2 primer for p21

<400> SEQUENCE: 17
gggcttcctc ttggagaaga tc                                             22
```